(12) United States Patent
Marciani

(10) Patent No.: US 10,195,257 B2
(45) Date of Patent: Feb. 5, 2019

(54) VACCINE FORMULATIONS COMPRISING QUILLAJA DESACYLSAPONINS AND BETA AMYLOID PEPTIDES OR TAU PROTEIN TO INDUCE A TH2 IMMUNE RESPONSE

(71) Applicant: Qantu Therapeutics, Inc., Lewisville, TX (US)

(72) Inventor: Dante J. Marciani, Lewisville, TX (US)

(73) Assignee: Qantu Therapeutics, Inc., Lewisville, TX (US)

( * ) Notice: Subject to any disclaimer, the term of this patent is extended or adjusted under 35 U.S.C. 154(b) by 0 days.

(21) Appl. No.: 14/908,446

(22) PCT Filed: Jul. 25, 2014

(86) PCT No.: PCT/US2014/048254
§ 371 (c)(1),
(2) Date: Jan. 28, 2016

(87) PCT Pub. No.: WO2015/017280
PCT Pub. Date: Feb. 5, 2015

(65) Prior Publication Data
US 2016/0166663 A1   Jun. 16, 2016

Related U.S. Application Data

(60) Provisional application No. 61/859,256, filed on Jul. 28, 2013.

(51) Int. Cl.
| | | |
|---|---|---|
| A61K 38/00 | (2006.01) | |
| A61K 49/00 | (2006.01) | |
| A61K 38/18 | (2006.01) | |
| A61B 5/00 | (2006.01) | |
| C07K 14/00 | (2006.01) | |
| C07K 16/00 | (2006.01) | |
| A61K 39/00 | (2006.01) | |
| C07K 14/435 | (2006.01) | |
| A61K 39/39 | (2006.01) | |

(52) U.S. Cl.
CPC .......... *A61K 39/0007* (2013.01); *A61K 39/39* (2013.01); *A61K 2039/545* (2013.01); *A61K 2039/55505* (2013.01); *A61K 2039/55577* (2013.01); *A61K 2039/57* (2013.01); *C07K 14/00* (2013.01); *C07K 16/00* (2013.01); *G01N 2800/28* (2013.01); *G01N 2800/2821* (2013.01); *G01N 2800/2828* (2013.01)

(58) Field of Classification Search
CPC .......... A61K 2300/00; A61K 39/39541; A61K 39/39; A61K 2039/55577; A61K 39/385; A61K 31/7024; A61K 2039/545; A61K 2039/55583; A61K 2039/57; A61K 2039/572; A61K 39/0007; A61K 39/39533; A61K 45/06; A61K 47/48023; A61K 47/48038; A61K 2039/505; A61K 2039/6087; A61K 39/3955; C07H 15/256; C07H 3/06; C07K 2317/76
See application file for complete search history.

(56) References Cited

U.S. PATENT DOCUMENTS

| | | | | |
|---|---|---|---|---|
| 5,229,490 | A | 7/1993 | Tam | |
| 5,443,829 | A * | 8/1995 | Kensil | .................... A61K 31/70 424/765 |
| 5,958,980 | A | 9/1999 | Rhodes | |
| 5,977,081 | A * | 11/1999 | Marciani | ................ A61K 39/39 424/184.1 |
| 6,080,725 | A * | 6/2000 | Marciani | ................ A61K 39/39 424/184.1 |
| 6,231,859 | B1 | 5/2001 | Kensil | |
| 6,262,029 | B1 * | 7/2001 | Press | ..................... C07J 63/008 424/184.1 |

(Continued)

FOREIGN PATENT DOCUMENTS

| | | |
|---|---|---|
| EP | 1009429 A1 | 6/2000 |
| EP | 1420815 B1 | 8/2006 |

(Continued)

OTHER PUBLICATIONS

Liu et al. Vaccine, 2002; 20: 2808-2815.*
Pawson et al. 2003, Science 300:445-452.*
Bowie et al. Science, 1990, 247:1306-1310.*
Burgess et al. J of Cell Bio. 1990, 111:2129-2138.*
Ghochikyan et al. Vaccine; 2006; 24:2275-2282.*
Boche et al. Acta Neuropathol. 2010; 120:369-384.*
Town, CNS Neurol. Disord. Drug Targets; 2009; 8: 114-127.*
Agadjanyan, M.G., et al., "Prototype Alzheimer's Disease Vaccine Using the Immunodominant B Cell Epitope from β-Amyloid and Promiscuous T Cell Epitope Pan HLA DR-Binding Peptide," Journal of Immunology 174(3):1580-1586, American Association of Immunologists, United States (2005).

(Continued)

*Primary Examiner* — Chang-Yu Wang
(74) *Attorney, Agent, or Firm* — Sterne, Kessler, Goldstein & Fox P.L.L.C.

(57) ABSTRACT

The present invention relates to compositions and methods for the prevention and treatment of neurodegenerative diseases, such Alzheimer's disease, that are caused by misfolding, aggregating proteins. The compositions and methods of the present invention comprise a vaccine formulation comprising an antigen selected from the group consisting of i) amyloid-β or a peptide that has in its amino acid sequence part of the amyloid-β amino acid sequence, ii) hyperphosphorylated tau protein or one of its hyperphoshorylated peptides, or iii) a combination of antigens derived from groups i) and ii) and that are formulated with a non-acylated or deacylated, natural or synthetic, bidesmosidic triterpene glycoside carrying an aldehyde or ketone group, which acts as an adjuvant or immune agonist. These vaccine formulations are capable of stimulating a Th2 immunity or antibody response against antigens such as amyloid-β and tau derived antigens, but not a Th1 immune response.

7 Claims, 9 Drawing Sheets

(56) References Cited

U.S. PATENT DOCUMENTS

| | | |
|---|---|---|
| 6,524,584 B2 | 2/2003 | Kensil |
| 6,645,495 B1 | 11/2003 | Kensil et al. |
| 6,719,970 B1 | 4/2004 | Costantino et al. |
| 6,719,978 B2 | 4/2004 | Schiller et al. |
| 6,787,637 B1 | 9/2004 | Schenk |
| 6,861,057 B2 | 3/2005 | Gaudernack et al. |
| 6,905,686 B1 | 6/2005 | Schenk |
| 6,964,769 B2 | 11/2005 | Sebbel et al. |
| 7,067,133 B2 | 6/2006 | Nicolau |
| 7,264,810 B2 | 9/2007 | Renner et al. |
| 7,279,165 B2 | 10/2007 | Bachmann et al. |
| 7,320,793 B2 | 1/2008 | Renner et al. |
| 7,371,572 B2 | 5/2008 | Schiller et al. |
| 7,479,280 B2 | 1/2009 | Schiller et al. |
| 7,494,656 B2 | 2/2009 | Bachmann et al. |
| 7,588,766 B1 | 9/2009 | Schenk |
| 7,713,942 B2* | 5/2010 | Dalsgaard .............. A61K 39/39 424/283.1 |
| 7,875,450 B2 | 1/2011 | Schiller et al. |
| 8,012,936 B2 | 9/2011 | Sigurdsson et al. |
| 8,022,180 B2 | 9/2011 | Mattner et al. |
| 8,034,348 B2 | 10/2011 | Schenk et al. |
| 8,034,353 B2 | 10/2011 | Yano et al. |
| 8,232,373 B2 | 7/2012 | Wang |
| 8,318,687 B2 | 11/2012 | Tabira et al. |
| 8,758,764 B2* | 6/2014 | Masignani ......... C07K 16/1232 424/185.1 |
| 8,808,692 B2* | 8/2014 | Kensil .................. A61K 31/704 424/130.1 |
| 9,334,313 B2* | 5/2016 | Masignani ......... C07K 16/1232 |
| 2002/0037290 A1* | 3/2002 | Armen ................ A61K 9/0019 424/178.1 |
| 2002/0094335 A1 | 7/2002 | Chalifour et al. |
| 2002/0197258 A1 | 12/2002 | Ghanbari et al. |
| 2003/0118635 A1* | 6/2003 | Dalsgaard .............. A61K 39/39 424/450 |
| 2003/0190333 A1* | 10/2003 | Mossman ............. A61K 31/739 424/234.1 |
| 2003/0228279 A1* | 12/2003 | Mossman ............. A61K 39/39 424/93.2 |
| 2004/0141984 A1 | 7/2004 | Bachmann et al. |
| 2004/0185057 A1* | 9/2004 | Kirkby .................. A61K 39/00 424/185.1 |
| 2005/0191310 A1 | 9/2005 | Kensil et al. |
| 2006/0148732 A1* | 7/2006 | Gutterman ............ A61K 31/20 514/33 |
| 2006/0210555 A1* | 9/2006 | Kensil .................. A61K 31/704 424/133.1 |
| 2007/0135337 A2 | 6/2007 | Chalifour et al. |
| 2008/0193470 A1* | 8/2008 | Masignani ......... C07K 16/1232 424/185.1 |
| 2009/0202627 A1 | 8/2009 | Nicolau |
| 2009/0246170 A1* | 10/2009 | Inoue ................. A61K 38/2026 514/1.1 |
| 2009/0246215 A1 | 10/2009 | Bachmann et al. |
| 2010/0062011 A1 | 3/2010 | Yano et al. |
| 2011/0002949 A1 | 1/2011 | Savage et al. |
| 2011/0020226 A1* | 1/2011 | Dalsgaard .............. A61K 39/39 424/9.1 |
| 2011/0064749 A1* | 3/2011 | Kensil .................. A61K 31/704 424/174.1 |
| 2011/0162093 A1* | 6/2011 | Ueda ..................... C07K 16/00 800/4 |
| 2011/0177109 A1* | 7/2011 | Smith, III .......... C07K 14/4711 424/185.1 |
| 2011/0182928 A1 | 7/2011 | Hoogerhout et al. |
| 2011/0206706 A1 | 8/2011 | Eisenbach-Schwartz et al. |
| 2011/0206742 A1 | 8/2011 | Blackburn et al. |
| 2011/0262458 A1 | 10/2011 | Sarasa |
| 2012/0014987 A1 | 1/2012 | Matsumoto |
| 2012/0052086 A1 | 3/2012 | Terakawa et al. |
| 2012/0315321 A1 | 12/2012 | St. George-Hyslop et al. |
| 2012/0321694 A1* | 12/2012 | Larocque ............... A61K 9/127 424/450 |
| 2012/0328605 A1* | 12/2012 | Larocque ............... A61K 9/127 424/133.1 |
| 2013/0011431 A1 | 1/2013 | Ulrich et al. |
| 2014/0294849 A1* | 10/2014 | Larocque ............... C07K 16/18 424/139.1 |
| 2014/0356389 A1* | 12/2014 | Masignani ......... C07K 16/1232 424/190.1 |
| 2016/0244489 A1* | 8/2016 | Masignani ......... C07K 16/1232 |

FOREIGN PATENT DOCUMENTS

| | | |
|---|---|---|
| EP | 2173375 A1 | 4/2010 |
| WO | WO-2013020722 A2 | 2/2013 |
| WO | WO-2015017280 A1 | 2/2015 |

OTHER PUBLICATIONS

Asuni, A.A., et al, "Immunotherapy Targeting Pathological Tau Conformers in a Tangle Mouse Model Reduces Brain Pathology With Associated Functional Improvements," The Journal of Neuroscience 27(34):9115-9129, Society for Neuroscience, United States (2007).

Asuni, A.A., et al., "Vaccination of Alzheimer's Model Mice with Aβ Derivative in Alum Adjuvant Reduces Aβ Burden without Microhemorrhages," The European Journal of Neuroscience 24(9):2530-2542, Wiley-Blackwell, France (2006).

Avila, J., "Intracellular and Extracellular Tau," Frontiers in Neuroscience 4:49, 4 Pages, Frontiers Research Foundation, Switzerland (2010).

Bach, P., et al., "Vaccination With Aβ-displaying Virus-like Particles Reduces Soluble-and Insoluble Cerebral Aβ and Lowers Plaque Burden in App Transgenic Mice," Journal of Immunology 182(12):7613-7624, American Association of Immunologists, United States (2009).

Boutajangout, A., et al., "Immunotherapy Targeting Pathological Tau Prevents Cognitive Decline in a New Tangle Mouse Model," The Journal of Neuroscience 30(49):16559-16566, Society for Neuroscience, United States (2010).

Boutajangout, A., et al., "Passive Immunization Targeting Pathological Phospho-tau Protein in a Mouse Model Reduces Functional Decline and Clears Tau Aggregates From the Brain," Journal of Neurochemistry 118(4):658-667, Wiley on behalf of the International Society for Neurochemistry, England (2011).

Cao, C., et al., "Successful Adjuvant-Free Vaccination of BALB/c Mice with Mutated Amyloid β Peptides," BMC Neuroscience 9:25, 11 Pages, BioMed Central, England (2008).

Chackerian, B., "Virus-like Particle Based Vaccines for Alzheimer Disease," Human Vaccines 6(11):926-930, Landes Bioscience, United States (2010).

Chai, X., et al., "Passive Immunization With Anti-Tau Antibodies in Two Transgenic Models: Reduction of Tau Pathology and Delay of Disease Progression," The Journal of Biological Chemistry 286(39):34457-34467, American Society for Biochemistry and Molecular Biology, United States (2011).

Crews, L. and Masilah, E., "Molecular Mechanisms of Neurodegeneration in Alzheimer's Disease," Human Molecular Genetics 19(R1):R12-R20, IRL Press at Oxford University Press, England (2010).

Daines, A.M., et al, "Mannosylated Saponins Based on Oleanolic and Glycyrrhizic Acids. Towards Synthetic Colloidal Antigen Delivery Systems," Bioorganic & Medicinal Chemistry 17(14):5207-5218, Elsevier Ltd., England (2009).

Fisher, Y., et al., "T Cells Specifically Targeted to Amyloid Plaques Enhance Plaque Clearance in a Mouse Model of Alzheimer's Disease," PLoS One 5(5):e10830, Public Library of Science, United States (2010).

Fu, H.J., et al, "Amyloid-β Immunotherapy for Alzheimer's Disease," CNS & Neurological Disorders Drug Targets 9(2):197-206, Bentham Science, United Arab Emirates (2010).

(56) References Cited

OTHER PUBLICATIONS

Gandy, S., "The Role of Cerebral Amyloid β Accumulation in Common Forms of Alzheimer Disease," The Journal of Clinical Investigation 115(5):1121-1129, American Society for Clinical Investigation, United States (2005).

Gelinas, D.S., et al., "Immunotherapy for Alzheimer's Disease," Proceedings of the National Academy of Sciences USA 101(Suppl 2):14657-14662, National Academy of Sciences, United States (2004).

Ghochikyan, A., et al., "Prototype Alzheimer's Disease Epitope Vaccine Induced Strong Th2-type Anti-aβ Antibody Response With Alum to Quil a Adjuvant Switch," Vaccine 24(13):2275-2282, Elsevier Science, Netherlands (2006).

Gravina, S.A., et al., "Amyloid β Protein (Aβ) in Alzheimer's Disease Brain. Biochemical and Immunocytochemical Analysis with Antibodies Specific for forms ending at Aβ40 or Aβ42(43)," The Journal of Biological Chemistry 270(13):7013-7016, American Society for Biochemistry and Molecular Biology, United States (1995).

Hall, S.R. and Rhodes, J., "Schiff Base-mediated Co-stimulation Primes the T-cell-receptor-dependent Calcium Signalling Pathway in CD4 T Cells," Immunology 104(1):50-57, Blackwell Science Ltd., England (2001).

Holmes, C., et al., "Long-term Effects of $A\beta_{42}$ Immunisation in Alzheimer's Disease: Follow-up of a Randomised, Placebo-controlled Phase I Trial," Lancet 372(9634):216-223, Elsevier, England (2008).

Hoogerhout, P., et al., "A Cyclic Undecamer Peptide Mimics a Turn in Folded Alzheimer Amyloid β and Elicits Antibodies Against Oligomeric and Fibrillar Amyloid and Plaques," PLoS One 6(4):e19110, Public Library of Science, United States (2011).

International Search Report and Written Opinion for Application No. PCT/US2014/048254, ISA/US, Alexandria, Virginia, United States, dated Nov. 6, 2014, 8 pages.

Ittner, L.M., et al., "Dendritic Function of Tau Mediates Amyloid-β Toxicity in Alzheimer's Disease Mouse Models," Cell 142(3):387-397, Elsevier, Inc., United States (2010).

Jin, M., et al., "Soluble Amyloid β-protein Dimers Isolated From Alzheimer Cortex Directly Induce Tau Hyperphosphorylation and Neuritic Degeneration," Proceedings of the National Academy of Sciences of the USA 108(14):5819-5824, National Academy of Sciences, United States (2011).

Jozwik, A., et al, "Beta-Amyloid Peptides Enhance the Proliferative Response of Activated CD4+ CD28+ Lymphocytes from Alzheimer Disease Patients and From Healthy Elderly," PLoS One 7(3):e33276, Public Library of Science, United States (2012).

Kayed, R., "Anti-tau Oligomers Passive Vaccination for the Treatment of Alzheimer Disease," Human Vaccines 6(11);931-935, Landes Bioscience, United States (2010).

Kitazawa, M., er al., "Lipopolysaccharide-induced inflammation exacerbates tau pathology by a cyclin-dependent kinase 5-mediated pathway in a transgenic model of Alzheimer's disease," The Journal of Neuroscience 25(39):8843-8853, Society for Neuroscience, United States (2005).

Kolarova, M., et al., "Structure and Pathology of Tau Protein in Alzheimer Disease," International Journal of Alzheimer's Disease 2012: Article ID 732526, 13 pages, Hindawi, United States (2012).

Krishnamurthy, P.K., et al., "Mechanistic Studies of Antibody-mediated Clearance of Tau Aggregates Using an Ex Vivo Brain Slice Model," Front Psychiatry 2:59, 6 pages, Frontiers Research Foundation, Switzerland (2011).

Lemere, C.A., et al., "Novel Aβ Immunogens: is Shorter Better?," Current Alzheimer Research 4(4):427-436, Bentham Science, United Arab Emirates (2007).

Masters, C.L. and Selkoe, D.J., "Biochemistry of Amyloid β-Protein and Amyloid Deposits in Alzheimer Disease," Cold Spring Harbor Perspectives in Medicine 2(6):a006262, Cold Spring Harbor Laboratory Press, United States (2012).

Monsonego, A., et al., "Increased T Cell Reactivity to Amyloid β Protein in Older Humans and Patients With Alzheimer Disease," The Journal of Clinical Investigation 112(3):415-422, American Society for Clinical Investigation, United States (2003).

Naslund, J., et al., "Correlation Between Elevated Levels of Amyloid β-peptide in the Brain and Cognitive Decline," JAMA 283(12):1571-1577, American Medical Association, United States (2000).

Naslund, J., et al., "Relative Abundance of Alzheimer Aβ Amyloid Peptide Variants in Alzheimer Disease and Normal Aging," Proceedings of the National Academy of Sciences USA 91(18):8378-8382, National Academy of Sciences, United States (1994).

Neniskyte, U., et al., "Neuronal Death Induced by Nanomolar Amyloid β Is Mediated by Primary Phagocytosis of Neurons by Microglia," The Journal of Biological Chemistry 286(46):39904-39913, American Society for Biochemistry and Molecular Biology, United States (2011).

Nicoll, J.A., et al, "Neuropathology of Human Alzheimer Disease After Immunization With Amyloid-β Peptide: a Case Report," Nature Medicine 9(4):448-452, Nature Publishing Company, United States (2003).

Ongradi, J. and Kovesdi, V., "Factors That May Impact on Immunosenescence: an Appraisal," Immunity & Ageing 7:7, BioMed Central, England (2010).

Petrushina, I., et al., "Mannan-$A\beta_{28}$ Conjugate Prevents Aβ-Plaque Deposition, but Increases Microhemorrhages in the Brains of Vaccinated Tg2576 (APPsw) Mice," Journal of Neuroinflammation 5:42, BioMed Central, England (2008).

Pubchem. CID 101810. Jun. 24, 2005, pp. 1-4 (online], [retrieved on Oct. 5, 2016]. Retrieved from the Internet, URL: http://pubchem.ncbi.nlm.nih.gov/rest/chemical/quillaic+acid, p. 1, formula.

Pubchem. CID 60866. Aug. 8, 2005, pp. 1-4; [online], [retrieved on Oct. 5, 2016]. Retrieved from the Internet, URL: http://pubchem.ncbi.nlm.nih.gov/rest/chemical/qs21, p. 1, formula, p. 4, formula.

Quintanilla, R.A., et al., "Truncated Tau and Aβ Cooperatively Impair Mitochondria in Primary Neurons," Neurobiology of Aging 33(3):619.e25-619.e35, 17 Pages, Elsevier, United States (2012).

Robertson, J.M., et al., "D011.10 and OT-II T Cells Recognize a C-Terminal Ovalbumin 323-339 epitope," Journal of Immunology 164(9):4706-4712, American Association of Immunologists, United States (2000).

Sigurdsson, E.M., "Immunotherapy Targeting Pathological Tau Protein in Alzheimer's Disease and Related Tauopathies," Journal of Alzheimer's Disease 15(2):157-168, IOS Press, Netherlands (2008).

Sisodia, S.S., "Alzheimer's Disease: Perspectives for the New Millennium," The Journal of Clinical Investigation 104(19):1169-1170, American Society for Clinical Investigation, United States (1999).

Streit, W.J. and Xue, Q.S., "The Brain's Aging Immune System," Aging and Disease 1(3):254-261, JKL International, United States (2010).

Tabira, T., "Immunization Therapy for Alzheimer Disease: a Comprehensive Review of Active Immunization Strategies," The Tohoku Journal of Experimental Medicine 220(2):95-106, Tohoku University Medical Press, Japan (2010).

Town, T., "Alternative Aβ Immunotherapy Approaches for Alzheimer's Disease," CNS & Neurological Disorders Drug Targets 8(2):114-127, Bentham Science, United Arab Emirates (2009).

Tseng, S.Y. and Dustin, M.L., "T-cell Activation: a Multidimensional Signaling Network," Current Opinion in Cell Biology 14(5):575-580, Elsevier Science Ltd., England (2002).

Ubhi, K. and Masliah, E., "Recent Advances in the Development of Immunotherapies for Tauopathies," Experimental Neurology 230(2):157-161, Elsevier, Inc., United States (2011).

Wiessner, C., et al., "The Second-Generation Active Aβ Immunotherapy CAD106 Reduces Amyloid Accumulation in APP Transgenic Mice while Minimizing Potential Side Effects," The Journal of Neuroscience 31(25):9323-9331, Society for Neuroscience, United States (2011).

Wilcock, D.M. and Colton, C.A., "Anti-Aβ Immunotherapy in Alzheimer's Disease: Relevance of Transgenic Mouse Studies to Clinical Trials," Journal of Alzheimer's Disease 15(4):555-569, IOS Press, Netherlands (2008).

(56) References Cited

OTHER PUBLICATIONS

Wilcock, D.M., et al., "Diverse Inflammatory Responses in Transgenic Mouse Models of Alzheimer's Disease and the Effect of Immunotherapy on These Responses," ASN Neuro 3(5):249-258, Sage, United States (2011).
International Preliminary Report on Patentability for Application No. PCT/US2014/048254, International Bureau of WIPO, Switzerland, dated Feb. 2, 2014, 7 pages.
Geijtenbeek, T.B.H. and Gringhuis, S.I., "Signalling through C-type lectin receptors: shaping immune responses," *Nature Reviews* 9: 465-479, Macmillan Publishers Limited, United States (2009).
Kensil, C.R., et al.," Structure/Function Studies on QS-21, A Unique Immunological Adjuvant from *Quillaja saponaria,*" *Saponins Used in Traditional and Modern Medicine*:165-172, Platinum Press, United States (1996).
Press, J.B., et al., "Structure/Function Relationships of Immunostimulating Saponins," *Studies in Natural Products Chemistry* 24:131-174, Elsevier, United States (2000).
Wisniewski, T., and Konietzko, U., "Amyloid-β immunisation for Alzheimer's disease," *The Lancet Neurology* 7:805-811, Elsevier B.V., The Netherlands (2008).
Partial European Search Report dated Mar. 16, 20.17 in European Patent Application No. 14832793.5, filed Jul. 25, 2014.
Akira, S., et al., "Pathogen Recognition and Innate Immunity," Cell 124(4):783-801, Cell Press, United States (2006).
Bomford, R., et al., "Adjuvanticity and ISCOM Formation by Structurally Diverse Saponins," Vaccine 10(9):572-577, Elsevier Science, Netherlands (1992).
Chackerian, B., et al., "Virus and Virus-like Particle-based Immunogens for Alzheimer's Disease Induce Antibody Responses Against Amyloid-βWithout Concomitant T Cell Responses," Vaccine 24(37-39):6321-6231, Elsevier Science, Netherlands (2006).
Feili-Hariri, M., et al, "Polarization of Naive T Cells Into Th1 or Th2 by Distinct Cytokine-driven Murine Dendritic Cell Populations: Implications for Immunotherapy," Journal of Leukocyte Biology 78(3):656-664, Society for Leukocyte Biology, United States (2005).
Finkelman, F.D., et al., "IFN-Gamma Regulates the Isotypes of Ig Secreted During in Vivo Humoral Immune Responses," Journal of Immunology 140(4):1022-1027, American Association of Immunologists, United States (1988).
Germann, T., et al., "Interleukin-12 Profoundly up-regulates the Synthesis of Antigen-specific Complement-fixing IgG2a, IgG2b and IgG3 Antibody Subclasses in Vivo," European Journal of Immunology 25(3):823-829, Wiley-VCH, Germany (1995).
Gilman, S., et al., "Clinical Effects of Abeta Immunization (AN1792) in Patients with AD in an Interrupted Trial," Neurology 64(9):1553-1562, Lippincott Williams & Wilkins, Minneapolis (2005).
Higuchi, R., et al., "An Acylated Triterpenoid Saponin from Quillaja Saponaria," Phytochemistry 27(4):1165-1168, Elsevier Ltd, Netherlands (1988).
Higuchi, R., et al., "Structure of Desacylsaponins Obtained From the Bark of Quillaja Saponaria," Phytochemistry 26(1):229-235, Elsevier Ltd, Netherlands (1987).
Huang, H.C. and Jiang, Z.F., "Accumulated Amyloid-β Peptide and Hyperphosphorylated Tau Protein: Relationship and Links in Alzheimer's Disease," Journal of Alzheimer's Disease 16(1):15-27, IOS Press, Netherlands (2009).
Iwasaki, A. and Medzhitov, R., "Regulation of Adaptive Immunity by the Innate Immune System," Science 327(5963):291-295, American Association for the Advancement of Science, United States (2010).
Kensil, C.R., et al., "Separation and Characterization of Saponins With Adjuvant Activity From Quillaja Saponaria Molina Cortex," Journal of Immunology 146(2):431-437, American Association of Immunologists, United States (1991).
Kensil, C.R., et al., "QS-21 and QS-7: Purified Saponin Adjuvants," Developments in Biological Standardization 92:41-47, Karger, Switzerland (1998).
Kensil, C.R., et al., "Structural and Immunological Characterization of the Vaccine Adjuvant QS-21," Pharmaceutical Biotechnology 6:525-541, Chapter 22, Plenum Press, United States (1995).
Lemere, C.A., "Developing Novel Immunogens for a Safe and Effective Alzheimer's Disease Vaccine," Progress in Brain Research 175:83-93, Elsevier, Netherlands (2009).
Liu, G., et al., "QS-21 Structure/function Studies: Effect of Acylation on Adjuvant Activity," Vaccine 20(21-22):2808-2815, Elsevier Science, Netherlands (2002).
Marciani, D.J., et al., "Altered Immunomodulating and Toxicological Properties of Degraded Quillaja Saponaria Molina Saponins," International Immunopharmacology 1(4):813-818, Elsevier Science, Netherlands (2001).
Marciani, D.J., et al., "Development of Semisynthetic Triterpenoid Saponin Derivatives With Immune Stimulating Activity," Vaccine 18(27):3141-3151, Elsevier Science, Netherlands (2000).
Marciani, D.J., et al., "Fractionation, Structural Studies, and Immunological Characterization of the Semi-synthetic Quillaja Saponins Derivative GPI-0100," Vaccine 21(25-26):3961-3971, Elsevier Science, Netherlands (2003).
Marciani, D.J., et al., "Genetically-engineered Subunit Vaccine Against Feline Leukaemia Virus: Protective Immune Response in Cats," Vaccine 9(2):89-96, Elsevier Science, Netherlands (1991).
Marciani, D.J., et al., "Vaccine Adjuvants: Role and Mechanisms of Action in Vaccine Immunogenicity," Drug Discovery Today 8(20):934-943, Elsevier Science, Netherlands (2003).
Mondino, A. and Jenkins, M.K., "Surface Proteins Involved in T Cell Costimulation," Journal of Leukocyte Biology 55(6):805-815, Society for Leukocyte Biology, United States (1994).
Moore, M.W., et al., "Introduction of Soluble Protein Into the Class I Pathway of Antigen Processing and Presentation," Cell 54(6):777-785, Cell Press, United States (1988).
Petrushina, I., et al., "Alzheimer's Disease Peptide Epitope Vaccine Reduces Insoluble but Not Soluble/oligomeric Aβ Species in Amyloid Precursor Protein Transgenic Mice," The Journal of Neuroscience 27(46):12721-12731, Society for Neuroscience, United States (2007).
Pullen, G.R., et al., "Antibody Avidity Determination by ELISA using Thiocyanate Elution," Journal of Immunological Methods 86(1):83-87, Elsevier, Netherlands (1986).
Rhodes, J., et al., "Therapeutic Potentiation of the Immune System by Costimulatory Schiff-base-forming Drugs," Nature 377(6544):71-75, Nature Publishing Group, England (1995).
Rosenmann, H., et al., "Tauopathy-like Abnormalities and Neurologic Deficits in Mice Immunized With Neuronal Tau Protein," Archives of Neurology 63(10):1459-1467, American Medical Assn, United States (2006).
Schenk, D., et al., "Current Progress in Beta-amyloid Immunotherapy," Current Opinion in Immunology 16(5):599-606, Elsevier Ltd., Netherlands (2004).
Schenk, D., et al., "Immunization with Amyloid-β Attenuates Alzheimer-Disease-like Pathology in the PDAPP Mouse," Nature 400(6740):173-177, Nature Publishing Group, England (1999).
Selkoe, D.J., "Toward a Comprehensive Theory for Alzheimer's Disease. Hypothesis: Alzheimer's Disease Is Caused by the Cerebral Accumulation and Cytotoxicity of Amyloid β-protein," Annals of the New York Academy of Sciences 924:17-25, Wiley-Liss, United States (2000).
Smith-Garvin, J.E., et al., "T Cell Activation," Annual Review of Immunology 27:591-619, Annual Reviews Inc, United States (2009).
Soltysik, S., et al., "Structure/function Studies of QS-21 Adjuvant: Assessment of Triterpene Aldehyde and Glucuronic Acid Roles in Adjuvant Function," Vaccine 13(15):1403-1410, Elsevier Science, Netherlands (1995).
Southwell, A.L. and Patterson, P.H., "Antibody Therapy in Neurodegenerative Disease," Reviews in the Neurosciences 21(4):273-287, De Gruyter, Germany (2010).
Troquier, L., et al., "Targeting Phospho-Ser422 by Active Tau Immunotherapy in the THYTau22 Mouse Model: A Suitable Therapeutic Approach," Current Alzheimer Research 9(4):397-405, Bentham Science, United Arab Emirates (2012).
Verdoliva, A., et al., "Simplified β-Amyloid Peptides for Safer Alzheimer's Vaccines Development," Human Vaccines 6(11):936-947, Landes Bioscience, United States (2010).

(56) References Cited

OTHER PUBLICATIONS

Yao, S., et al., "Triterpenoid Saponins from the Roots of Gypsophila Paniculata," Chinese Journal of Natural Medicines 8(1):28-33, Verlag Helvetica Chimica Acta AG, Zürich, Switzerland (2010).

Younkin, S.G., "Evidence That Aβ42 Is the Real Culprit in Alzheimer's Disease," Annals of Neurology 37(3):287-288, American Neurological Association, United States (1995).

Marciani, D.J., et al., "New Th2 adjuvants for preventive and active immunotherapy of neurodegenerative proteinopathies," *Drug Discovery Today* 19(7): 912-920, Elsevier Ltd., The Netherlands (Jul. 2014).

Marciani, D.J., "A New Sole Th2 Antiinflammatory Immunomodulator for Alzheimer's," *Drug Discovery & Development*, 11 pages, Advantage Business Media, Apr. 11, 2016, accessed at http://www.dddmag.com/articles/2016/04/new-sole-th2-anti-inflammatory-immunomodulator-alzheimers, accessed on Jan. 23, 2017.

Marciani, D.J., "Alzheimer's disease vaccine development: A new strategy focusing on immune modulation," *Journal of Neuroimmunology* 287: 54-63, Elsevier B.V., The Netherlands (Oct. 2015).

Marciani, D.J., "A retrospective analysis of the Alzheimer's disease vaccine progress—The critical need for new development strategies," *J Neurochem.* 137(5): 687-700, International Society for Neurochemistry, United States (Jun. 2016).

Marciani, D.J., "Is fucose the answer to the immunomodulatory paradox of Quillaja saponins?" *Int Immunopharmacol.* 29(2): 908-13, Elsevier B.V., The Netherlands (Dec. 2015).

\* cited by examiner

VACCINE FORMULATIONS COMPRISING QUILLAJA DESACYLSAPONINS AND BETA AMYLOID PEPTIDES OR TAU PROTEIN TO INDUCE A TH2 IMMUNE RESPONSE

FIELD OF THE INVENTION

The present invention relates to immune modulatory formulations or vaccines that induce a strong Th2 immune response with production of antibodies against the proteins β-amyloid (Aβ), hyperphosphorylated tau protein and/or its peptides, peptide analogs and peptide conjugates, alone or in combinations, but do not induce a Th1 immune response. In particular, this invention pertains to vaccines containing non-acylated bidesmosidic aldehyde-carrying triterpene glycosides as adjuvants or immune agonists, that stimulate Th2 immunity with antibody production, but do not elicit Th1 inflammatory immune response with or without the production of cytotoxic T lymphocytes (CTLs), and that are useful in the treatment and/or prevention of Alzheimer's disease and other neurodegenerative diseases that are proteinopathies.

BACKGROUND OF THE INVENTION

Alzheimer's Disease, β-Amyloid Protein and Tau Protein

Neurodegenerative diseases, although caused by a variety of factors, share a certain common characteristic. In effect, many of these illnesses are proteinopathies or diseases caused by misfolded, aggregating proteins (Southwell A L et al. *Rev Neurosci.* 21:273-287, 2010). One such degenerative disorder is Alzheimer's disease (AD), a progressive neurodegenerative disease that affects largely the elderly population leading to dementia; while by age 65 the AD prevalence in this population is 7-10%, it increases severely to about 40% in the population over 80 years of age (Sisodia S S. *J Clin Invest.* 104:1169-1170, 1999; Fu, H J et al. *CNS Neurol Disord Drug Targets.* 9:197-206, 2010).

The significance 01 this disease is highlighted by the World Health Organization's prediction that by the year 2050, AD would be the world's leading cause of death. A characteristic of AD is the deposition of the protein Aβ into clumps called oligomers on neural cells to form extracellular neuritic plaques, which seem to play a crucial role in its pathology (Crews L et al. *Hum Mol Genet.* 19:R12-R20, 2010; Gandy S. *J Clin Invest.* 115:1121-1129, 2005; Neniskyte U. et al. *J Biol Chem.* 286:39904-39913, 2011). In effect, the main neuropathological symptoms of AD associated with a progressive cognitive decline are the extracellular accumulation of Aβ plaques, the intracellular formation of neurofribrillary-like structures (NFTs) composed of paired helical filaments with phosphorylated tau proteins (Selkoe D J. *Ann N.Y. Acad Sci.* 924:17-25, 2000), and the neuronal and synaptic loss. Most Aβ consist of two isoforms, a main peptide called Aβ40 that contains amino acid residues from 1 to 40 and a minor one that is less than 5% of the Aβ, which has 2 extra amino acids, ending at residue 42 instead of 40, and which is named "long Aβ" or Aβ42 (Naslund J. et al. *Proc Nat Acad Sci USA.* 91:8378-8382, 1994). While both Aβ isoforms have a propensity to form β-sheets, because the long Aβ isoform, Aβ42, has more aggregability than Aβ40, it, is believed that it starts the process leading to the formation of oligomers, fibrils and plaques (Gravina S A. et al. *J Biol Chem.* 1270:7013-7016, 1995; Younkin S G. *Ann Neurol.* 37:287-288, 1995). Indeed, it has been proposed that these aggregated states of Aβ are those with the most potent neurotoxicity and responsible for AD. Support for this proposal is provided by the prion diseases, e.g. Creutzfeldt-Jakob disease, where the misfolding of amyloidogenic peptides leads to neurotoxicity, but without plaque formation (Gandy S. *J Clin Invest.* 115:1121-1129, 2005).

Although it is unclear if the accumulation of Aβ is either the decisive neurotoxic end-product or a by-product of an independent metabolic lesion that happens to be neurotoxic, the removal of Aβ plaques by certain immunological methods have shown a recovery of cognitive functions in a transgenic mouse model for AD (Schenk D. et al. *Curr Opin Immunol.* 16:599-606, 2004; Wilcock D M. et al. *J Alzheimer's Dis.* 15:555-569, 2008). After these results were reported using a vaccine having Aβ42 and the adjuvant QS-21, formulation AN-1792, (Schenk D. et al. *Nature* 400:173-177, 1999) (U.S. Pat. No. 6,905,686 B1), several groups confirmed and extended those studies concerning the effects of active immune therapy in preventing deposition of Aβ and improving the cognitive functions in a mouse transgenic model (see Tabira T. *Tohoku J Exp Med.* 220:95-106, 2010; Wilcock D M. et al. *ASN Neuro.* 3:249-258, 2011; Chackerian B. *Hum Vaccin.* 6:926-230, 2010; Wiessner C. et al. *J Neurosci.* 31:9323-9331, 2011).

While the results from a transgenic mouse model were encouraging from both the therapeutic and safety aspects, clinical studies using AN-1792 were terminated due to the meningoencephalitis triggered by the vaccine in 6% of the patients during a Phase II clinical trial. Evidently, this side effect was the result of a cell mediated inflammatory response caused by the combination of certain epitopes from the antigen Aβ42 (Gelinas D S et al. *Proc Nat Acad Sci USA.* 101:14657-14662, 2004) and the QS-21 adjuvant, which elicits Th1 immunity with production of cytotoxic lymphocytes or CTLs (Kensil C R et al. *Dev Biol Stand.* 92:41-47, 1998). In fact, autopsy of a patient immunized with AN-1792 showed the presence of T-lymphocyte meningoencephalitis and infiltration of cerebral white matter by macrophages (Nicoll J A et al. *Nature Med.* 9:448-452, 2003).

Nonetheless, a subsequent evaluation of the patients enrolled in that study, showed that those that developed antibodies against Aβ42 may have benefited cognitively from the vaccine (Gilman S et al. *Neurology* 64:1553-1562, 2005). While autopsies of some of the study participants showed a decrease in Aβ plaques, it has been difficult to establish a correlation between this decrease and improvement of cognitive functions (Holmes C. et al. *Lancet* 372:216-223, 2008). A more controlled study to minimize contamination by plaque Aβ has shown a strong con elation between the levels of Aβ and cognitive status (Naslund J. et al. *JAMA* 83:1571-1577, 2000). These results are more in line with those reported for the transgenic mouse model. An outcome of these reported studies has been a surge of activity trying to develop active and passive immunization methods targeting Aβ, in order to prevent or reduce the plaques load in the brain.

Another protein closely associated with AD is the tau protein, a microtubule associated protein that stabilizes the microtubule structure that in the adult brain is present in six isoforms, which are characterized by unusually high ratios of hydrophilic amino acids and proline. These six isoforms differ according to their content of i) tubulin binding domain repeats, i.e. 3 or 4 repeats of 31 to 32 amino acids in the C-terminal part of tau, and ii) number of specific inserts of 29 amino acids each, in the N-terminal region of the protein (Kolarova M. et al. *Int J Alzheimer's Dis.* 2012:732526, 2012). Tau isoforms vary in size from 352 to 442 amino acid residues. Results of this amino acid composition are its high solubility and the lack of a strict secondary structure with the peptide chain being in a random coil state (Huang H C et al. *J Alzheimer's Dis,* 16:15-27, 2009). Most tau isomers are found at axons, with only a few located at neuronal cytoplast and dendritic cells.

Tau's functionality is tightly regulated by its degree of phosphorylation, with too much or too little phosphorylation altering its conformation and affecting its biological functions (Ubhi K et al. *Exp Neurol.* 230:157-161, 2011). In pathological conditions tau is hyperphosphorylated, which results in a decrease of its binding to microtubules and the presence of isolated tau in the neurons; the isolated tau being susceptible to form paired helical filaments when 8 to 10 of the at least 30 available sites are phosphorylated. However, it has been proposed that to cause pathological changes, tau hyperphosphorylation must be at specific sites, but not others (Avila J. *Front Neurosci.* 4:49, 2010). Different studies indicate that in tau paired helical filaments the dominant structure is β-sheet, a structure that can contribute to conformational changes in that protein and its aggregation, which play a key role in its neuronal toxicity by forming intracellular NFTs (Kolarova M. et al. *Int J Alzheimers Dis.* 2012:732526, 2012). These neurodegenerative disorders caused by the tau protein's conformational alterations are known as tauopathies, with AD being the most prevalent.

A body of evidence indicates that formation of pathological tau conformers seems to occur with or after the initiation of Aβ aggregation and induction of neurotoxicity. Support for this concept is given by the fact that Aβ dimers isolated from the brains of late-onset AD patients and at subnanomolar concentrations are enough to induce hyperphosphorylation of tau at epitopes that are AD-relevant, initiating a disruption of the microtubule cytoskeleton and causing neuritic damage (Ming J et al. *Proc Nat Acad Sci USA.* 108:5819-5824, 2011).

However, studies with knockout and transgenic mice seem to indicate that the induction of AD may be the result of a combination of factors, which include conformational defects in Aβ, tau and perhaps some other proteins. In effect, it has been proposed that accumulation of Aβ in neurons may induce tau phosphorylation by alternative pathways, in agreement with reports showing that Aβ dimers can induce hyperphosphorylation. It has been also shown in transfected primary neurons that expression of truncated tau resulted in mitochondrial fragmentation in these cells, which was aggravated by exposure of the cells to sub-lethal concentrations of Aβ; results that indicate some kind of cooperation between those proteins (Quintanilla R A et al. *Neurobiol Aging.* 33(3):619. e25-35, 2012).

Therefore, it is becoming more accepted that the toxicity of Aβ is tau dependent. For instance, it has been shown that in transgenic mice expressing a truncated form of tau (Δtau) or with an absence of tau ($tau^{-/-}$) and Aβ-forming, memory deficits are prevented and have an improved survival rate as compared to mice producing the normal tau protein (Ittner L M et al. *Cell* 142:387-397, 2010). Results that indicate that tau confers at least some of Aβ toxic properties. Thus, it now more accepted that AD may be a result of damage caused by cooperative effects between Aβ and tau; while, these 2 proteins seem to be crucial for starting AD, it is possible that other proteins may also play a role.

Similar to Aβ, because the tau protein's pathological effects seem to be the result of conformational changes, it is a suitable candidate for passive and/or active immune therapy, where the defective isoforms are removed by interactions with specific antibodies, this way reducing the extracellular Aβ neuritic plaques and intracellular tau NFTs. Indeed, it has been shown that immunization of a transgenic mouse for a tau mutant that develops early NFTs, with the peptide Tau379-408[P-$Ser_{396,404}$] plus aluminum phosphate as an adjuvant, produced tau-antibodies that recognized the intracellular NFTs, reducing the aggregated tau in the brain and slowing the progression of the tangle-related behavioral phenotype (Asuni A A et al. *J Neurosci.* 27:9115-9129, 2007; Sigurdsson E M. *J Alzheimer's Dis.* 15:157-168, 2008; U.S. Pat. No. 8,012,936 B2; US 2002/0197258 A1). The fact that these tau-antibodies are attached to NFTs, shows that in addition to passing across the blood-brain barrier (BBB), they can also penetrate the cell; yet, these antibodies could not cross the BBB in wild type mice, indicating some deterioration of this barrier caused by neurodegenerative diseases. Similar results have been reported in transgenic mice expressing Tau22 and that were immunized against the pathological epitope phosphor-Ser422 combined with CFA (Troquier L. et al. *Curr Alzheimer Res.* 9:397-405, 2012). The results indicate that active immunization resulted in Tau clearance and the improvement of cognitive deficits caused by tau pathology.

Additional proof of the potential therapeutic efficacy of tau vaccines comes from vaccination with the peptide Tau379-408[P-$Ser_{396,404}$] of transgenic mice htau/PS1, model that has an early onset and more aggressive progression of tau pathology than the htau model (Boutajangout A. et al. *J Neurosci.* 30:16559-16566, 2010). In this model, the results show that vaccination totally prevents severe cognitive impairment.

An explanation for the antibody-mediated clearance of tau aggregates has been obtained using an ex-vivo brain slice model. FITC labeled anti-tau antibodies show that i) the antibodies were localize on the phosphorylated tau, ii) are co-localized with markers of the endosomal/lysosomal pathway and iii) the tau-antibody complex were found together in an enriched lysosome fraction, indicating that antibody-mediated clearance of intracellular tau aggregates seems to occur via the lysosomal pathway (Krishnarnurthy P K et al. *Front Psychiatry* 2011; 2:59). Similar results to those obtained by vaccination have been attained by the administration of monoclonal antibodies against tau epitopes that are relevant for its pathogenic properties. Administration of antibodies against tau pathological forms to transgenic mice showing a progressive tauopathy, resulted in a reduction of tau pathology and prevention of tau intracellular buildup (Chai X et al. *J Biol Chem.* 286:34457-34467, 2011). Another group reported similar results using a mAb that targets the pathological phospho-tau protein, a treatment that resulted in decrease of both tau pathology and functional impairments in a transgenic mouse model (Boutajangout A. et al. *J Neurochem.* 118:658-667, 2011).

Although the immunotherapy approach for treatment of tauopathies has been focused on the hyperphosphorylated tau, some groups have proposed that tau oligomers, i.e. aggregates between the size of monomers and NFTs, should be the target of immunotherapy. The bases for this proposition is the evidence that neuronal loss precedes NFTs formation and that tau oligomers can cause neurodegeneration and memory impairment in the absence of Aβ (Kayed R. *Hum Vaccin.* 6:931-935, 2010). Yet, that immunization with the full-length tau resulted in a severe autoimmune reaction, mules out the use of soluble tau as an immunogen and stresses the need for identification of epitopes highly specific for early tau damage. Hence, the available data shows that immunotherapy producing antibodies that target different tau protein structures is a viable option in AD treatment, possible in conjunction with immunotherapy of Aβ because of the apparent synergism between Aβ and tau pathological effects.

The Immune System

Vertebrates exhibit both non-specific immunity (also referred to as innate immunity) and specific immunity (also referred to as acquired or adaptive immunity). Innate immunity ligands, which are pathogens' products, upon recognition by receptors encoded in the animal's genome trigger a defensive response involving cytokine production, activation of complement and natural killer cells and the identification and removal of foreign substances by specialized white blood cells; i.e. these ligands are exogenous adjuvants or immune agonists (Akira S et al. *Cell* 124:793-801, 2006).

Innate immunity may also start the specific humoral and cell-mediated immunities, carried out by B and T lymphocytes together with other cells. B cells participate in humoral immunity or Th2 immunity when activated to produce antibodies by antigen presenting cells (APCs) and CD4+Th2 helper T cells (Iwasaki A et al. *Science* 327:291-295). The Th2 immunity is characterized by the production of non-cytolytic antibodies and anti-inflammatory cytokines. Cell-mediated immunity or Th1 immunity, involves cytokine production by Th1 helper T cells, activation of macrophages and antigen-specific CD8+ cytotoxic T-cells (CTLs) to destroy pathogens. Activation of CD4+ and CD8+ T cells requires two signals: one derived from the T cell receptor (TCR) interaction with antigen-major histocompatability (MHC) complexes on APCs, and the second a co-stimulatory signal delivered by CD80 or CD86 ligands (also known as B7-1 and, B7-2, respectively) on the APCs when binding to the CD28 surface receptor on T cells (Smith Garvin J et al. *Annu Rev Immunol.* 27:591-619, 2009). The result of a concerted stimulation with CD80 is Th1 immunity with the production of pro-inflammatory cytokines and CTLs that are crucial to destroy tumor and virally infected cells (Feili-Hariri M et al. *J Leukoc Biol.* 78:656-664, 2005).

Immunization with the Aβ42/QS-21 vaccine formulation of transgenic mice and patients in the Phase 1 clinical studies elicited a Th2 immune response, while the patients in the Phase 2 clinical studies exhibited a Th1 immune response. However, the vaccine formulation used in the Phase 2 clinical studies that elicited Th1 immunity was not identical to the one used either in the mouse model or the Phase 1 clinical studies, which elicit Th2 immunity. The difference between both formulations was that the one that elicited Th1 immunity contained a non-ionic detergent, polysorbate-80, presumably to aid the manufacturing process and stability of Aβ42; in contrast, the formulation that elicited a Th2 immunity was lacking the detergent (Schenk D. et al. *Curr Opin Immunol.* 16:599-606, 2004).

Thus, as a result of the active immune therapy results, a great deal of activity has been devoted to design new peptide antigens related to Aβ and denominated here "Aβ-derived peptides" to maximize the production of anti-Aβ antibodies, while restricting the Th1 immune response. For instance, shorter Aβ-derived peptides lacking T-cell epitopes have been used in vaccines that in the transgenic mouse model produced antibodies that either pass across the BBB and reduced the levels of insoluble Aβ or act as a peripheral sink by clearance of circulating Aβ (Petrushina I. et al. *J Neurosci.* 27:12721-12731, 2007; Lemere C A et al. *Curr Alzheimer Res.* 4:427-436, 2007; Lemere C A. *Prog Brain Res.* 175:83-93, 2009; Verdoliva A et al. *Hum Vaccin.* 6:963-947, 2010, Fu H J et al. *CNS Neurol Disord Drug Targets,* 9:197-206, 2010).

A different tactic to induce only a Th2 immune response has been the use of mutated Aβ (Cao C. et al. *BMC Neurosci.* 9:25, 2008) and of cyclic peptides from Aβ (Hoogerhout P. et al. *PLoS One.* 6(4):e19110, 2011). These and other Aβ-derived peptides have been described in the following patents and patent application U.S. Pat. No. 6,787,637; U.S. Pat. No. 6,861,057; U.S. Pat. No. 7,067,133 B2; U.S. Pat. No. 7,588,766; U.S. Pat. No. 8,022,180 B2; U.S. Pat. No. 8,034,348 B2; U.S. Pat. No. 8,034,353 B2; US 2002/0094335 A1; EP 1420815 B1; 2007/0135337 A2; US 2009/0202627 A1; US 2010/0062011 A1; US 2011/0002949 A1; US 2011/0182928 A1; US 2011/0206706 A1; US 2011/0206742; US 2011/0262458 A1; US 2012/0052086 A1; 2012/0315321 A1). Other methods to elicit Th2 immunity against Aβ involve the use of DNA vaccines to express antigens similar to those indicated above (EP 2173375 A1; US 2012/0014987 A1), alone or in conjunction with a virus or a virus like particle (U.S. Pat. No. 6,719,970; U.S. Pat. No. 6,964,769; U.S. Pat. No. 7,264,810; U.S. Pat. No. 7,279,165; U.S. Pat. No. 7,479,280; U.S. Pat. No. 7,875,450; U.S. Pat. No. 7,8,318,687).

Similar to Aβ-based vaccines, tau-based vaccines apparently have the same restrictions about Th1 immunity. Administration to a transgenic mouse model for AD of lipopolysaccharide (LPS), a TLR4 ligand and known inducer of inflammation, resulted in activation of microglia and tau hyperphosphorylation, but it did not affect Aβ (Kitazawa M et al. *J NeuroSci.* 25:8843-8853, 2005). LPS exacerbated tau pathology via the kinase cdk5. Thus, it is apparent that any immune response in the CNS must be confined to Th2 immunity producing antibodies only. Another report showing the damaging effects of an inflammatory response on the CNS, is one in which full length tau was administered with CFA, a powerful Th1 inflammatory adjuvant. Vaccinated non-transgenic mice developed autoimmunity and showed the histopathologic features typical of AD and tauopathies, stressing the dangers of using full length tau with presumably T and B epitopes and a Th1 adjuvant (Rosenmann H et al. *Arch Neurol.* 63:1459-1467, 2006). Because of these results, it is obvious that tau-based vaccines must be formulated with only tau's B epitopes and without a Th1 adjuvant, like lipid A or CpG, to avoid stimulation of a damaging Th1 inflammatory response; situation that parallels that of the Aβ-based vaccines for the treatment or prevention of AD and that should be the norm for any vaccine that stimulates an immune response that acts on the CNS.

Due to the side-effects caused by a pro-inflammatory Th1 immune response, such as that elicited by QS-21 or lipid A, alternatives to stimulate only Th2 immunity to produce protective antibodies have been investigated, including other adjuvants, substitute administration modes, some delivery systems and different carriers.

One approach has been the use of Aβ40 without any adjuvant and administered intra-nasally, to produce antibodies against the amino acid sequence 1-15, recognized as the B-cell epitope. This immunization mode resulted in a Th2 immune response and reduced levels of Aβ plaques in transgenic mice (Town T. *CNS Neurol Disord Drug Targets.* 8:114-127, 2009).

Another group has used mutated Aβ peptides, but without an adjuvant to stimulate in mice Th2 immunity with antibody production, apparently with good results. Another method to avoid the inflammatory response has been the use of adjuvants that stimulate Th2 immunity with antibodies production. For instance, immunization of younger transgenic mice with Aβ42 without T-cell epitopes plus alum yielded an effective antibody response with reduction of Aβ burden but no cerebral microhemorrhages. Yet, that immune response did not occur in older mice, a deficient response that may be due to immunosenescence as well as the weak adjuvant used (Asuni A A et al. *Eur J Neurosci.* 24:2530-2542, 20061, a critical factor considering that AD affects predominantly the ageing population.

To boost the Th2 immune response stimulated, by alum, the switching of alum to Quil A, a preparation of quillaja saponins that contains QS-21, has been tried (Ghochikyan A et al. *Vaccine* 24:2275-2282, 2006). According to these authors, changing from alum to Quil A increases the antibodies levels without changing the Th2 antibodies profile; yet, there is a significant reduction of the IgG1/IgG2a ratio, a strong indicator of a Th1 biased immunity. While the discrepancy about the antibodies' profile can be explained by the fact that Quil A and QS-21, stimulate both Th1 and Th2 immunity, a reduced IgG1/IgG2a ratio after treatment with Quil A, shows that IFN-γ, a Th1 cytokine, is being secreted (Finkelman F D et al. *J Immunol.* 140:1022-1027, 1988). Also, the large increase in IgG2b reported after the switch to Quil A, indicates secretion of IL-12, a Th1 driving cytokine (Germann T et al. *Eur J Immunol.* 25:823-829, 1995).

Although it has been presumed that a switch from alum to Quil A does not induce Th1 immunity while enhancing the production of anti-Aβ antibodies, and thus proposed as a safe and beneficial treatment for AD patients (see Fu H J et al. *CNS Neurol Disord Drug Targets,* 9:197-206, 2010), it is possible that the change in immunity triggered by Quil A and leading to stimulation of Th1 immunity and down-regulation of Th2 immunity, may lead to undesirable autoimmune responses against the naturally occurring A. Other strategies involve the use of Aβ peptides that are B cell, epitopes and that are connected sequentially either to T cell epitope sequences unrelated to Aβ or are conjugated to a carrier protein that would, then stimulate the T cells, this way avoiding an anti-Aβ inflammatory response (Agadjanyan M G et al. *J Immunol.* 174:1580-1586, 2005; Verdoliva A et al. *Hum Vaccin.* 6:936-947, 2010). Conjugates of the polysaccharide mannan, a Th2 adjuvant, and an Aβ-derived peptide, Aβ$_{28}$, have been used to immunize APP transgenic mice; while the immunization produced antibodies that prevented Aβ-plaque deposition, it also increased the risk of microhemorrhages in the brains of vaccinated animals; apparently a result of the anti-Aβ antibodies stimulated by the mannan conjugate (Petrushina I et al. *J Neuroinflammation* 5:42, 2008) Several of these antigen constructs are the subject of issued patents or pending patent applications.

To prevent Th1 immunity while inducing an effective Th2 immune response with protective antibodies, Aβ-derived peptides that are B-cell epitopes have been expressed or covalently conjugated to virus like particles (VLP) derived from the *E. coli* phage Q β, which provides a scaffold to link the peptides as well as T-helper cell epitopes (Wiessner C et al. *J Neurosci.* 31:9323-9331, 2011; Chackeran B et al, *Vaccine* 24:6321-6331, 2006; U.S. Pat. No. 6,719,978 B2; U.S. Pat. No. 6,964,769; U.S. Pat. No. 7,264,810; U.S. Pat. No. 7,279,165; U.S. Pat. No. 7,320,793; U.S. Pat. No. 7,371,572 B2; U.S. Pat. No. 7,479,280 B2; U.S. Pat. No. 7,494,656; U.S. Pat. No. 7,875,450 B2; US 2004/0141984 A1; US 2009/0246215 A1; US 2013/0011431 A1). The use of VLPs apparently facilitates the production of antibodies against tolerogens or self-antigens, such as Aβ.

An alternative strategy has been the use of retrovirus-like particles having only the gag and pol proteins from murine leukemia virus, but displaying Aβ-peptides, i.e. Aβ retroparticles, to stimulate Th2 immunity against Aβ (Back P et al. *J Immunol.* 182:7613-7624, 2009).

In all cases, the vaccines have been designed to stimulate production of Th2 immunity with anti-Aβ antibodies that reduce the Aβ load, while avoiding Th1 immune pro-inflammatory responses, either without adjuvants or with adjuvants that elicit only Th2 immunity. Hence, most of the attention has been focused on the antigen rather than the adjuvant component; evidently a result of the inflammatory response observed during the phase 2 clinical studies with the Aβ vaccine AN-1792 containing QS-21. Of significance is that the Th1 inflammatory response took place only after modification of the original vaccine formulation by adding the non-ionic detergent polysorbate-80, for use in the phase 2 clinical studies; a response that has been explained by the exposure of Aβ T-cell epitopes due to the detergent combined with the use of an effective Th1 adjuvant. However, it is most likely that the main target of the detergent action was the QS-21 adjuvant rather than the antigen, i.e. it has been shown that addition of non-ionic detergents to QS-21, Quil A and other q. saponin analogs, causes a large enhancement of their adjuvanticity, 10-fold or more based on the IgG titers elicited in the absence and presence of polysorbate-80 (EP1009429 A1).

Thus, it is feasible that an incipient immune response, result of a supposedly suboptimal formulation, was magnified by the large increase in the QS-21 adjuvant activity. It is dubious that low concentrations of the non-ionic detergent polysorbate-80, would have significant effects on the Aβ structure; i.e. oligomeric Aβ can only be dissociated by using high concentrations of formic acid, strong chaotropic agents, like Gu.HCl, or detergents as sodium dodecyl sulfate (SDS) under stringent conditions (Masters C L et al. *Cold Spring Harb Perspect Med.* 2:a006262, 2012). However the use of Aβ-derived peptides lacking T-cell epitopes has confirmed that those epitopes, in combination with what it was apparently a "high dose" of QS-21, were responsible for the Th1 pro-inflammatory response.

Analogous to the Aβ vaccines constrains on stimulation of Th1 immunity, the tau vaccines that have shown beneficial results in transgenic mouse models for AD, are those with phosphorylated short tau peptides as immunogens, in some cases conjugated to carrier proteins. In contrast, tau vaccine formulations containing the full length tau plus a Th1 adjuvant, like LPS or CFA, stimulated a damaging inflammatory response. Yet, the alternative of using Aβ or tau-based vaccines without an effective adjuvant or one like alum, a Th2 adjuvant that stimulates IgG production but fails to stimulate an effective immune response in aged mice, presents a serious problem because in humans and some mammalians, the target populations for AD or AD-like conditions are the aged ones. This situation stresses the need for effective adjuvants in the AD vaccines to stimulate a beneficial Th2 immune response in the elderly while overcoming the effect of immune senescence and preventing tolerance.

Immune senescence or the deter-oration of the immune system linked to aging, is one of the main challenges to the development of vaccines for the elderly (Gruver A et al. *J Pathol.* 211:144-156, 2007; Ron-Harel N et al. *Trends Neurosci.* 32:367-375, 2009); Ongradi J et al. *Immun Ageing* 7:7, 2010). Aging affects APCs, i.e. dendritic cells and macrophages, by reducing the expression of toll-like-receptors (TLRs) associated with innate immunity (Aspinall R et al. *Immunity and Ageing* 4:9, 2007), and the co-stimulatory ligands CD80 and CD86 associated with adaptive immunity.

Another significant aging-related change is the decrease in expression of the CD28 receptor for the B7 ligands in CD8+ and CD4+ T cells (Plackett T P et al. *J Leukoc Biol.* 76:291-299, 2004); these reduced expressions of the APCs' co-stimulatory ligands and T cells' CD28 receptor, are major factors contributing to the immunity decline in the elderly, which leads to tolerance. Immune senescence also occurs in the brain, causing the microglia, which are the macrophages equivalent (Gemechu J M et al. *Front Cell Neurosci.* 6:38. 2012; Wrona D. *J Neuroimmunol.* 172:38-28, 2006; Streit W J et al. *Aging Dis.* 1:254-261, 2010), to function atypically and promote neurodegeneration (Luo X-G et al. *Mol Neurodegener.* 5:12, 2010). However, as the BBB acts as a filter that shields the brain from molecules and cells from the blood milieu, the brain is an immune privileged organ; thus, it is unlikely that Aβ or tau-derived antigens from vaccines would be processed by the brain's microglia. Hence, like other antigens, initial processing of tau or Aβ-derived antigens should take place at the APCs, with the subsequent secretion of Th1 or Th2 cytokines and interactions with T cells leading to T cell activation and production of CD4+ or CD8+ T cells, functions that can be modulated by different adjuvants (Marciani D J. *Drug Discov Today.* 8:934-943, 2003). While there is evidence that in AD the peripheral T cells, CD4+ and CD8+ T cells, can enter the brain and infiltrate areas with Aβ-plaques, T cells may also exert, their effects without entering the brain, via Th1 and/or Th2 cytokines, e.g. IFN-γ, TNF-α, IL-10, and other factors (Jozwik A et al. *PLoS One* 7(3):e33276, 2012; Fisher Y et al. *PLoS One* 5(5):e10830, 2010).

Thus, immune senescence may affect the immune system by blocking the production of cytokines by anergic peripheral T cells and imposing tolerance; a situation that may impact the production of protective antibodies. In fact, down regulation of the co-stimulatory APC ligands, CD80 and CD86, and/or their T cell's receptor CD28, by eliminating the required co-stimulatory signal causes T cell anergy (Mondino A et al. *J Leukoc Biol.* 53:805-815, 1994; Su-Yi T et al. *Current Opin Cell Biol.* 14:575-580, 2002). Because this condition may be common in the elderly AD population, it is unlikely that vaccines without an effective adjuvant or immune agonist would stimulate a useful protective antibody response against Aβ or tau protein in many of those patients. Essentially, the adjuvant(s) required for an AD vaccine would need to deliver an alternative T cell co-stimulatory signal to replace the one delivered by the down-regulated CD80/86 ligands to allow T cell activation and elicit only a Th2 immune response with production of protective antibodies, a task that adjuvants like IFA, alum and many others cannot deliver.

Saponin Adjuvants

The only well-characterized exogenous immune agonists or adjuvants that can deliver an alternative co-stimulatory signal are Quil A and its components, such as QS-21, QS-18, QS-17 and QS-7. Structurally, these quillaja saponins are glycosides that have as an aglycone a lipophilic triterpene, which is linked to two oligosaccharide chains bound at positions C-3 and C-28. Because of the presence of both hydrophilic and lipophilic structures, saponins have an amphipathic character with detergent-like properties. It is due to these properties and that the triterpene can insert into the cholesterol of the membrane's lipid bilayer, that quillaja saponins have a translocating capacity, i.e. allow the passage of proteins across the cellular membranes, such as the cell and endosomal membranes, directly into the cytosol.

Most of these saponins, with the exception of QS-7 that is acetylated, have their fucosyl residue acylated with an acyl-acyloyl moiety composed of two 3,5-dihydroxy-6-methyloctanoic acid residues linked in tandem (R Higuchi et al. *Phytochemistry* 26:229-235, 1987; ibid, 27:1165-1168, 1988) and de-acylation occurs under mild conditions, i.e. above pH 6 and at room temperature (RT), a situation that apparently results in a loss of these saponins' capacity to insert and pass across the cell's membrane, to deliver an antigen directly into the APC's cytosol to trigger CTL production. Structure/function studies have shown that the aldehyde group is essential to stimulate immunity and that its modification results in a loss of the immune stimulatory capacity (Soltysik S et al. *Vaccine* 13:1403-1410, 1995). In effect, synthetic mannosylated triterpene glycosides based on oleanolic and glycyrrizhic acids that lack an aldehyde group, do not show immunological activity (Dairies A M et al. *Bioorg Med Chem.* 17:5207-5218, 2009), a result of the lack in those glycosides of a group capable of providing a co-stimulatory signal to the T cells. In fact, from a variety of triterpene saponins, only those carrying an aldehyde group, i.e. Quillaja saponins, >*Gypsophila* saponins and *Saponaria* saponins, have adjuvant activity (Bomford R et al. *Vaccine* 10:572-577, 1992). Furthermore, it is evident that the lipophilic acyl moiety of quillaja saponins is also required for stimulation of Th1 immunity with CTL production, as de-acylated quillaja saponins or DS-QS (FIG. 1) stimulate Th2 immunity without CTLs (Marciani D J et al. *Int. Immunopharmacol.* 2001; 1:813-818; Liu G et al. *Vaccine* 20:2808-2815, 2002).

Hence, it is apparent that an acyclic alkyl chain, bound to the triterpene is essential to allow its passage, together with the antigen, across the cell and endosomal membranes for processing by the endogenous pathway, a requirement to yield Th1 immunity with CTL production (Marciani D J et al. *Vaccine* 21:3961-3971, 2003). Of relevance is that while a small co-stimulatory Schiff-base-forming drug, 4-(2-formyl-3-hydroxyphenoxymethyl benzoic acid) or tucaresol (Rhodes J et al. Nature 377:71-75, 1995; U.S. Pat. No. 5,958,980), favors a Th1-biased immunity with a Th1-type cytokine profile and concomitant CTL production, DS-QS and other non-acylated aldehyde carrying saponins stimulate Th2 immunity. Important for an AD vaccine is that while DS-QS stimulates a Th2 immunity, because of its aldehyde group still has the capacity to deliver to T cells the co-stimulatory signal needed for their activation and prevent anergy (Hall S R et al. *Immunology* 104:50-57, 2001).

Moreover, the Th2 immune response seems to be independent of the presence or absence of T cell epitopes in the antigen, i.e. while mice immunized with, ovalbumin (OVA) plus QS-21 or Quil A developed a Th1 immune response with the concomitant production of OVA-specific CTLs, mice immunized with OVA and DS-QS develop a Th2 immune response without either CTL production (Marciani D J et al. *Int. Immunopharmacol.* 2001; 1:813-818) or secretion of IFN-γ. Though OVA has a peptide sequence, $OVA_{323-339}$, which has multiple overlapping T cell epitopes and MHC-binding registers (Robertson J M et al. *J Immunol.* 164:4607-4712, 2000), immunization with DS-QS failed to elicit Th1 immunity and CTL production; in contrast, immunization with the acylated glycosides Quil A or QS-21 plus OVA, stimulated both a strong Th1 immunity and OVA-specific CTL production.

These results show that DS-QS and similar natural or synthetic non-acylated saponins modulate the immune response against OVA in a manner independent of the presence of T cell epitopes in the antigen. In fact, saponins that have small acyl groups like acetyls, e.g. QS-7 (U.S. Pat. No. 6,231,859 B1) (FIG. 2), behave to some degree similar to DS-QS. However, QS-7 at higher doses stimulates the production of antigen-specific CTLs (U.S. Pat. Nos. 6,231,859 B1; 6,524,584 B2), indicating that some degree of acylation is required for these glycosides to stimulate Th1 immunity.

SUMMARY OF THE INVENTION

The present invention is directed to vaccine formulations for the prevention or treatment of Alzheimer's disease, a disease of the elderly characterized by the deposition of Aβ plaques on neural cells in the brain and intracellular accumulation of hyperphosphorylated tau in the form of NFTs in the same cells, leading to their death and other neurodegenerative diseases. Some antibodies produced against the Aβ and tau proteins after passing across the BBB can break and interfere with the formation of plaques or NFTs respectively, or alternatively, they can act as a peripheral sink outside the CNS, clearing the circulating Aβ, this way removing the burden from neural cells. Thus, an Aβ or tau-specific antibody response or Th2 immune response, may be beneficial to prevent or stop the disease; however, an inflammatory immune response or Th1 immune response can be damaging to the neural cells. Currently, several vaccines have been proposed in which Aβ-derived antigens having only B-cell epitopes are formulated without or with adjuvants that stimulate only Th2 immunity, such as alum. A similar approach has been also use with some tau-derived peptide vaccines in transgenic mouse models for AD. A major problem with that approach is that AD occurs largely in the elderly population that due to the aging process suffers of immune senescence, a condition characterized by the loss of receptors and ligands on APCs and T cells, which lead to T cell anergy or tolerance. Hence, an effective Aβ or tau-based vaccine should besides stimulating Th2 immunity, ameliorate the effects of immune senescence; a condition that antigen-alone vaccines or formulated with currently available Th2 adjuvants, or DNA vaccines expressing the antigen alone or as part of a larger protein or a VLP, it is doubtful that they would be able to overcome.

The present invention ameliorates those deficiencies due to immune senescence by in addition to stimulating only Th2 immunity with production of anti-Aβ or anti-tau antibodies, even in the presence of T cell epitopes, delivers an alternative co-stimulatory signal needed for T cell activation; an objective that is achieved by formulating the Aβ or tau-derived antigens with one or more non-acylated bidesmosidic triterpene glycosides or saponins that carry an aldehyde or ketone group. These glycosides that act as adjuvants or immune agonists, in addition to providing a T cell co-stimulatory signal via their aldehyde or ketone group, would allow the antigen processing required for stimulation of Th2 immunity with production of anti-Aβ or anti-tau antibodies, but, without the stimulation of Th1 immunity.

In one embodiment, the present invention can be used as a preventive vaccine to elicit the production of anti-Aβ or anti-tau-antibodies, or both types of antibodies, which would later either avert or slow down the formation of Aβ plaques and NFTs in the brain's cells, thus preventing or delaying the onset of AD while reducing its severity. In another embodiment, the present invention can be used as therapeutic vaccine to elicit the production of antibodies against Aβ or tau, or both antigens, that would bind and disrupt the Aβ deposited as plaques in the brain or the intracellularly NFTs in the neurons, improving the prognosis of the disease.

DETAILED DESCRIPTION OF THE INVENTION

Figure 1:
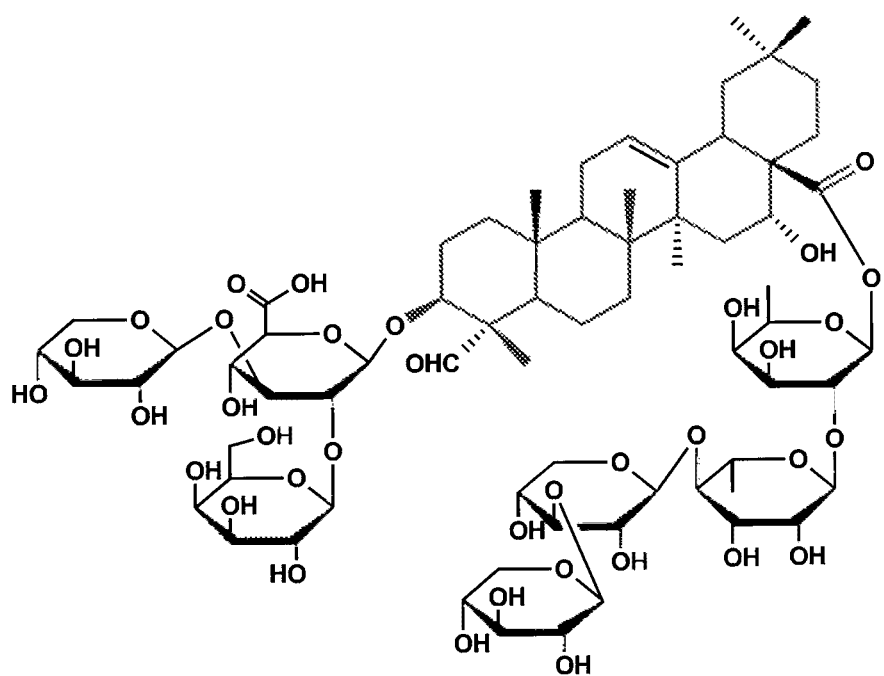
FIG. 1 shows the structure of DS-QS having a trisaccharide at C-3 and where the acyl-acyloyl group has been removed from the fucosyl residue at C-28 by mild alkaline hydrolysis.
Figure 2:
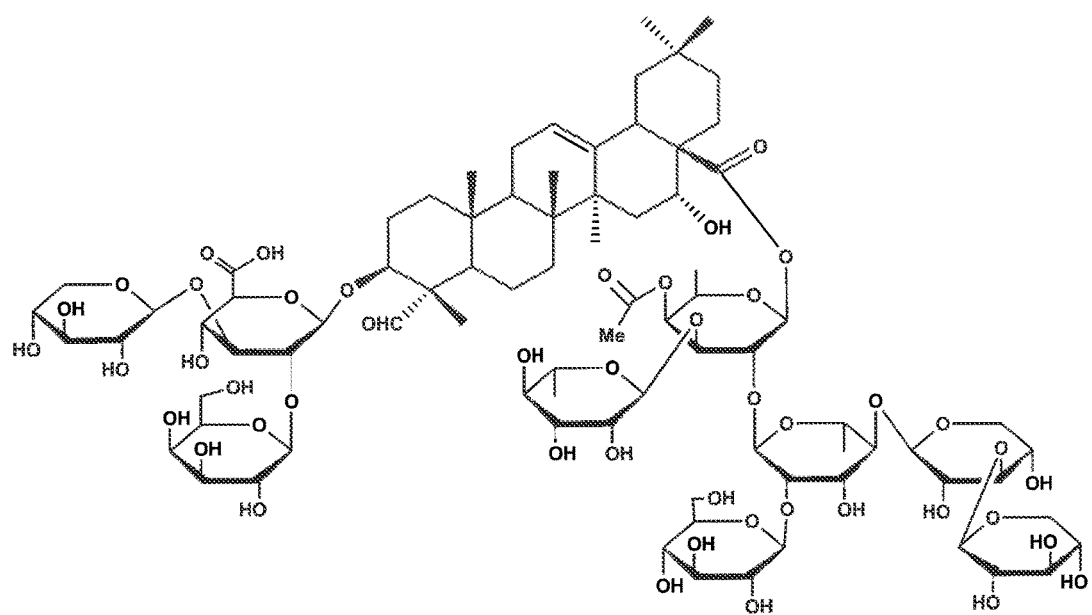
FIG. 2 shows the structure of QS-7 that has an acetyl group at the fucosyl residue bound at C-28 of the triterpene.

As far as it is known, the only proposed use for DS-QS has been that of an excipient for saponin adjuvants, such as QS-7, QS-18 and QS-21, but not as an adjuvant (U.S. Pat. No. 6,645,495 B1). In publication US 2005/0191310 A1, the use of QS-7 as an adjuvant is proposed once more, but only when administered with certain excipients described in the application, DS-QS being one of the proposed excipients. Consequently, that DS-QS can elicit an effective Th2 immunity and not act just, as an excipient, has important implications for AD vaccines, where a Th2 immunity is required to avoid damage to the CNS, but, there is also a critical need to deliver a co-stimulatory signal to compensate for the immune senescence's detrimental effects on the APCs and T cells. Because of immune senescence, the need to counterbalance the effects associated with aging is not limited to sub-unit antigen vaccines, but it also applies to DNA and VLP vaccines.

In effect, there are two unrelated events associated with the later vaccines, the first would be the expression by engineered cells of the antigen, either as a protein or incorporated in a VLP, and the second would be the response that the immune system would mount against the newly expressed antigen(s). While it is unlikely that antigen expression induced by DNA and VLP vaccines would be affected by aging, the immune response would be impacted by the immune system performance, which deteriorates as a result of the aging process. Thus, the use of natural or synthetic non-acylated bidesmosidic triterpene saponins carrying an aldehyde or ketone group would be advantageous for AD vaccines, such as Aβ or tau-based, because of the i) stimulation of a polarized Th2 immunity that is independent of the presence of T cell epitopes in the antigen, ii) amelioration, of the immune senescence's effects by delivering an alternative co-stimulatory signal that prevents T cell anergy, iii) their very low toxicity and iv) a good stability that would assure a long shelf life.

The methods of the present invention comprise of administering to an individual for preventive or therapeutic purposes a vaccine formulation composed of an Aβ or tau-derived antigen, or a combination of both types of antigens, which can be synthetic, produced by recombinant DNA technology or natural product, and that is selected from the group consisting of i) Aβ-protein (1-40), (1-42) and (1-43); ii) Aβ-protein (1-40), (1-42) and (1-43), but without the dominant T cell epitope sequences 16-33 and/or 28-42 (Monsonego A et al. *J Clin Invest.* 112:415-422, 2003); iii) Aβ-peptide (1-15) carrying the Aβ-protein B cell epitopes; iv) Aβ-peptide (1-6) carrying a dominant B cell epitope, v) full length tau protein, vi) a peptide derived from the amino acid sequence of the tau protein and that is or is not phosphorylated. In one preferred embodiment the peptides are either free or linked covalently to a carrier selected from the group consisting of a i) protein like KLH, tetanus toxoid, edestin or albumin; ii) multiple antigenic peptide system or MAP (U.S. Pat. No. 5,229,490), such as a linear or branched oligolysine core; iii) peptide, like the linear PADRE T helper epitope (U.S. Pat. No. 8,232,373); v) Liposome (US 2009/0202627 A1; 2011/0076323 A1) and v) viral like particle, such as a bacteriophage, tobacco mosaic virus (TMS) or adenovirus. In another preferred embodiment, the Aβ or tau-derived antigens, free or conjugated to a carrier, are formulated with a natural or synthetic saponins or saponin analogs carrying an aldehyde or ketone group, that is non-acylated or de-acylated, and that is selected from the group consisting of i) de-acylated quillaja saponins, DS-QS; ii) de-acylated saponins from *Silene jenissensis*; iii) squarroside A; iv) non-acylated saponins from *Gypsophila* sp. and v) other non-acylated bidesmosidic triterpene saponins that are equal or similar to DS-QS, such as those saponins from *Saponaria* sp. and other plant species. The formulation is substantially free from acylated saponin or acylated saponin analogs. As discussed above, when practicing this embodiment, it is important to employ a vaccine or formulation that includes an adjuvant that stimulates Th2 immunity but stimulates substantially no Th1 immune response. Therefore, the presence of more than minor amounts of acylated saponin or acylated saponin analog is to be avoided.

The present invention is also directed to pharmaceutical and veterinary compositions comprising of one or mote non-acylated bidesmosidic triterpene glycosides or saponins carrying an aldehyde or ketone group, and one or more pharmaceutically acceptable diluents, carriers or excipients. These compositions may be employed as immune potentiators of Th2 immunity in animals and humans.

The present invention is also directed to preventive or therapeutic vaccines comprising one or more Aβ or tau-derived antigens, or combinations of both, and one or more non-acylated bidesmosidic triterpene glycosides or saponins having an aldehyde or ketone group.

The present invention is also directed to a method of eliciting and enhancing prophylactically or therapeutically a Th2 immune response in a mammal, comprising of administering an effective amount of one or more non-acylated bidesmosidic triterpene glycosides or saponins carrying an aldehyde or ketone group, to enhance the immune response of a mammal to one or more Aβ or tau-derived antigens, either separately or in combination.

The present invention is also directed to a method of preventive or therapeutic vaccination, comprising administering one or more Aβ or tau-derived antigens, or combinations of both types of antigens, and one or more non-acylated bidesmosidic triterpene glycosides or saponins having an aldehyde or ketone group.

The present invention is also directed to a method of preventive or therapeutic vaccination, comprising of one or more Aβ or tau-derived antigens, either separately or combinations of both, and non-acylated bidesmosidic triterpene glycosides or saponins having an aldehyde or ketone group, that can be administered parenterally, such as subcutaneous, intramuscular or intraperitoneal injection; mucosally, such as nasally, sublingually or rectally; and transdermally, such as by electroporation and transdermal patch.

DETAILED DESCRIPTION OF THE PREFERRED EMBODIMENTS

A first aspect of the invention is directed to a vaccine formulation for human or veterinary use, comprising
 (a) one or more antigens selected from the groups consisting of a amyloid-β derived antigens and a tau-derived antigen, and
 (b) one or more triterpene saponins adjuvants, wherein
  (1) an aldehyde or ketone group is present on the triterpene aglycone core structure of the triterpene saponin,
  (2) linear or branched oligosaccharides are attached to positions 3 and 28 of the triterpene aglycone core structure, and
  (3) the glycosyl residues of the oligosaccharide at position 28 are non-acylated.

In a second aspect of the invention, the triterpene saponin adjuvant is selected from the group consisting of
 (1) Quillaja desacylsaponin, having a 3-glucuronic acid residue, a quillaic acid as triterpene aglycone core with an aldehyde group at position 4, and lacking an acyl group on the oligosaccharide at the position 28 of the triterpene aglycone,
 (2) *Gypsophila* sp. saponins, having a 3-glucuronic acid residue, a gypsogenin as triterpene aglycone core with an aldehyde group at position 4, and lacking an acyl group on the oligosaccharide at position 28 of the triterpene aglycone,
 (3) *Acanthophyllum* sp. saponins, having a 3-glucuronic acid residue, a gypsogenin as a triterpene aglycone core with an aldehyde group at position 4, and lacking an group on the oligosaccharide at position 28 of the triterpene aglycone,
 (4) *Saponaria* sp. saponins having a 3-glucuronic acid residue, a gypsogenin as triterpene aglycone core with an aldehyde group at position 4, and lacking an acyl group on the oligosaccharide at position 28 of the triterpene aglycone, and (6) Saponins from *Silene jenisseensis* having a 3-glucuronic acid residue, a quillaic acid as triterpene aglycone core with an aldehyde group at position 4, and lacking an acyl group on the oligosaccharide at the position 28 of the triterpene aglycone, A third aspect of the invention is directed to the vaccine formulation of aspect 2, wherein the 3-glucuronic acid residue is either alone or linked to a linear or branched oligosaccharide having from one to four glycosyl residues.

A fourth aspect of the invention is directed to a vaccine formulation of aspect 2 or 3, wherein the oligosaccharide at position 28 is a linear or branched oligosaccharide having from two to seven glycosyl residues.

A fifth aspect of the invention is directed to a vaccine formulation of aspects 1, 2, 3 or 4 wherein one or more of the triterpene saponins is natural, semi-synthetic or synthetic.

A sixth aspect of the invention is directed to a vaccine formulation of any of aspects 1 through 5, wherein said amyloid-β derived antigen is a peptide having the amino acid sequence corresponding to amino acid residues 1 to 40 or 1 to 42.

A seventh aspect of the invention is directed to a vaccine formulation of claim of any of aspects 1 through 5, wherein said amyloid-β derived antigen is a peptide having one or more amino acid sequences found in the amino acid sequence of 1 to 42.

An eighth aspect of the invention is directed to a vaccine formulation of aspect 7, wherein said amyloid-β derived antigen is a peptide covalently linked to a carrier, such as a peptide, a protein, a viral like particle, a liposome, an immune stimulating complex (ISCOM), or a nanoparticle formed by cross-linked sugars.

A ninth aspect of the invention is directed to a vaccine formulation of any of aspects 1 through 5, wherein said tau protein derived antigen is a peptide having the amino acid, sequence corresponding to residues 1 to 352 or 1 to 441 from one of six tau isoforms.

A tenth aspect of the invention is directed to a vaccine formulation of aspect 9, wherein said tau-derived antigen is a peptide that, is phosphorylated at serine, threonine or tyrosine amino acid residues.

An eleventh aspect of the invention is directed to a vaccine formulation of aspect 10, wherein said tau-derived antigen is a peptide covalently linked to a carrier, such as a peptide, protein, viral like particle, liposome, ISCOM or a nanoparticle formed by cross-linked sugars.

A twelfth aspect of the invention is directed to a vaccine formulation of aspect 5, further comprising a pharmaceutically acceptable carrier, diluent or another Th2 adjuvant.

A thirteenth aspect of the invention is directed to a method of vaccinating a subject, comprising administering the vaccine of aspect 7 to said subject to potentiate a Th2 immune response in said subject to said antigen.

A fourteenth aspect of the invention is directed to a method of vaccinating a subject, comprising administering the vaccine of aspect 8 to said subject to potentiate a Th2 immune response in said subject to said antigen.

A fifteenth aspect of the invention is directed to a method of vaccinating a subject, comprising administering the vaccine of aspect 10 to said subject to potentiate a Th2 immune response in said subject to said antigen.

A sixteenth aspect of the invention is directed to a method of vaccinating a subject, comprising administering the vaccine of aspect 11 to said subject to potentiate a Th2 immune response in said subject to said antigen.

As discussed above, vaccine formulations are substantially free of acylated saponins or acylated saponin analogs. Preferably, the vaccine formulations have less that 5%, less than 4%, less than 3%, less than 2%, less than 1% or less than 0.5% by weight of acylated saponins or acylated saponin analogs based upon total weight of saponin or saponin analog.

Vaccine: As used herein, the term "vaccine" refers to a formulation which contains the composition of the present invention and which is in a form that is capable of being administered to an animal, preferably a human. Typically, the vaccine comprises a conventional saline or buffered aqueous solution medium in which the composition of the present invention is suspended or dissolved. In this form, the composition of the present invention can be used conveniently to prevent, ameliorate, or otherwise treat a condition. Upon introduction into a host, the vaccine is able to provoke an immune response.

Vaccine compositions of the invention comprise, or alternatively consist of, an immunologically effective amount of the inventive immune enhancing composition together with a pharmaceutically acceptable diluent, carrier or excipient.

All patents and publications referred to herein are expressly incorporated by reference in their entirety.

EXAMPLES

The following examples are illustrative, but not limiting, of the compositions and methods of the present invention. Other suitable modifications and adaptations of the variety of conditions and parameters normally encountered and obvious to those skilled in the art are within the spirit and scope of the invention.

Example 1

De-Acylation of Quillaja Saponins (q. Saponins)

A q. saponins fraction containing the components from QS-16 to QS-21 is obtained by purification of an enriched q. saponins preparation prepared by extensive dialysis of an aqueous bark extract against water on a semi-preparative C-18 column. The different fractions obtained by stepwise elution with acetonitrile/water containing 0.1% TFA, are analyzed by HPLC using a Vydac C-4 column and an acetonitrile/water linear gradient containing 0.1% TFA (Kensil C R et al. *J Immunol.* 146:431-437, 1991) and those containing QS-16 to QS-21 are pooled. The solvent of these pooled fractions is evaporated and the syrupy residue dissolved in water and lyophilized. Alternatively, the whole QS preparation may be used Removal of the acyl group from the fucose of the C-28 oligosaccharide of the pooled q. saponins fraction can be accomplished by treatment with a solution of 0.2N sodium hydroxide in 90% 1-propanol (U.S. Pat. No. 5,443,829), or as described here with a solution of ammonium hydroxide in methanol (MeOH) (D J Marciani et al, *Vaccine* 2000; 18:314-3151), To 1 g of QS in a 100 nil, round bottom flask, add with stirring 30 mL of a 3 N ammonium hydroxide in 80% MeOH, the flask is close tightly and the stirring is continued for about 24 hours at RT. Filter out the insoluble materials from the cloudy solution using a fine glass filter paper, wash the insoluble residue with 7 mL of MeOH and pool the filtrate and wash. Monitor the de-acylation by HPLC using a Vydac C-4 column eluted with a water-acetonitrile (ACN) gradient with 0.1% TFA. Deacylation is complete when the original starting material's HPLC profile is replaced by a small number of peaks, about 4, that elute close to the front. The DS-QS have two oligosaccharide side-chains, a C-3 disaccharide or trisaccharide and a C-28 tetrasaccharide, pentasaccharide hexasaccharide, the major components with a mol. wt. (MW) of ~1,536 and 1,700, Evaporate the MeOH-ammonium hydroxide from the clear filtrate in a rotary evaporator or a centrifugal vacuum concentrator; dissolve the syrupy residue in 20 mL of de-ionized water, and evaporate again to remove residual MeOH. Dissolve the syrupy residue with 10-15 mL of de-ionized water and lyophilize it, to yield the DS-QS as an off-white powder. The yield is ~40 to 70% of the initial QS material and includes both the DS-QS and the fatty acids produced during deacylation. Dissolve the dry product in 12 mL of water, and adjust the pH to 3.8 with acetic acid; to this solution, add with mixing 12 mL of 1-propanol to yield a 50% concentration of the alcohol. Adsorb this solution to 2-2.5 g of silica gel (Lichropep Si60 or similar one) and evaporate the solvent under a gentle stream of dry nitrogen or under vacuum. Load the pre-adsorbed silica evenly on top of a silica gel column made of Lichropep Si60 or a similar one (2.5 cm ID×14 cm L; 70 mL) and elute by gravity with ~70 mL of 1-propanol, 3 column volumes of 85% 1-propanol, 2.5 column volumes of 80% 1-propanol and 75% 1-propanol respectively and 1 column volumes of 50% 1-propanol. Collect 30 mL fractions and analyze them by RP-HPLC to identify the different DS-QS components. Those corresponding to QS 18 and QS-21 and eluting together with the 75% 1-propanol, are evaporated in a centrifugal vacuum concentrator to remove the solvent, dissolved in water and lyophilized. The dry DS-QS, free of fatty acids and some other minor components, is stored at RT under vacuum and over a desiccant to remove any water from the preparation. The DS-QS purified fraction is analyzed by reverse phase HPLC on C-18 and its molecular weight profile determined by MALDI.

Example 2

Purification of Saponins from *Gypsophila* sp

Figure 3:
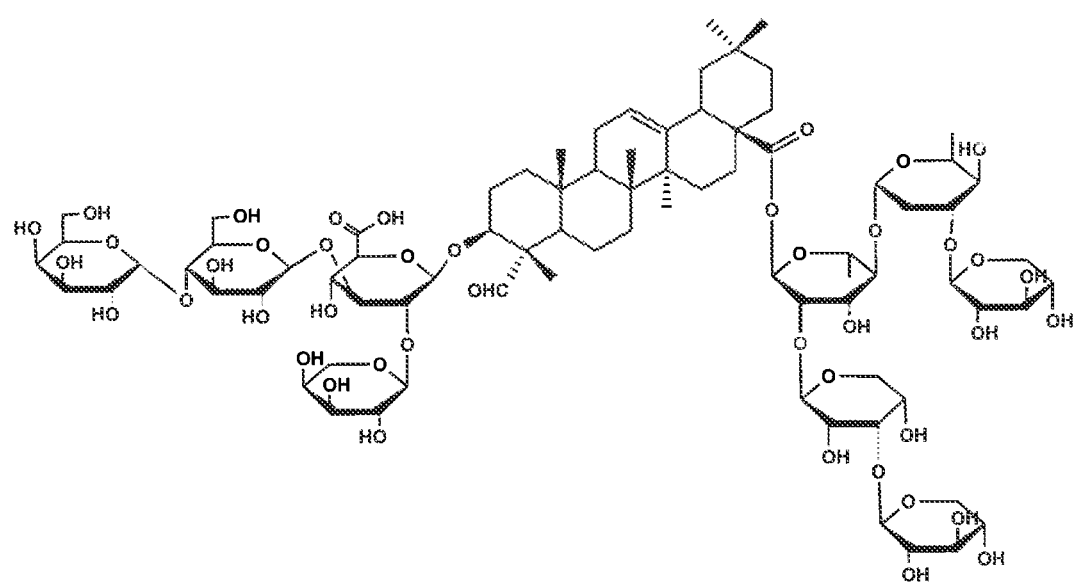
FIG. 3 shows the structure of a non-acylated bidesmosidic saponin from *Gypsophila paniculate* having gypsogenin as the aglycone, with a tetrasaccharide at C-3 and a pentasaccharide at C-28.

Five g of a crude preparation of *gypsophila* saponins are extracted with 100 mL of 75% ethanol (EtOH) for 4 hours under reflux, and the solvent is evaporated under vacuum in a rotary evaporator. Suspend the dry residue in ~75 mL of water and extract sequentially with 75 mL of EtOAc and 75 mL of n-butanol (n-BuOH); after shaking the n-BuOH and aqueous solution, the two solvents are allowed to separate overnight at RT. The n-BuOH phase that contains the bidesmosidic saponins, some of which may carry a p-methoxycinnamoyl residue (Yao S et al. *Chin J Nat Med.* 8:28-33, 2010), is evaporated under reduced pressure to recover the mixed saponins. The n-BuOH soluble saponins are fractionated by silica gel chromatography on Si 60, 230-400 mesh, equilibrated with chloroform/methanol/water, ($CHCl_3$/MeOH/$H_2O$), 100:10:1, the saponins sample is diluted in 35 ml of the same solvent, applied to the silica gel column, which is eluted stepwise, with 90:10:1, 80:10:1, 70:10:1, 60:10:1, 50:10:1, 40:10:1, 30:10:1, 20:10:1, 10:10:1, and finally pure MeOH. Analyze the fractions collected by HPLC using a C-18 column and a linear gradient of MeOH/water, 20% to 80% MeOH and monitored by measuring the absorbance at 210 nm. Pool those fractions containing specific saponins and determine their UV/VIS absorption spectra between 230 nm and 340 nm, samples showing absorbance peaks in this region are rejected due to the presence of p-methoxycinnamoyl residues in the saponins. Evaporate the solvent in a rotary evaporator and purify the saponins to homogeneity by using a preparative C-18 column eluted with a linear gradient of MeOH/water, from 20% to 80% MeOH. Pool the samples containing the saponin, evaporate the MeOH solvent under reduced pressure, dissolve the residue in water and lyophilize to obtain the purified *Gypsophila* saponin (FIG. 3). Determine the M.W. of each non-acylated bidesmosidic saponin component by MALDI.

Example 3

Figure 4:
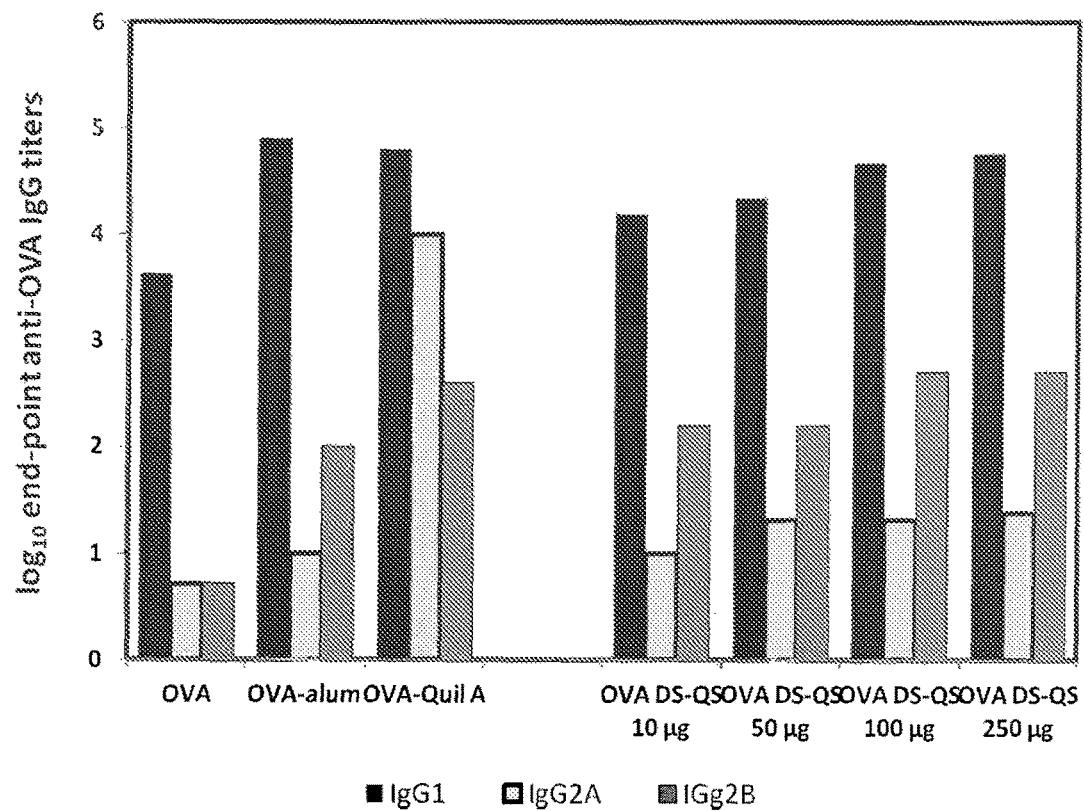
FIG. 4 shows the effects of increasing DS-QS doses in the administered vaccine formulations on the production of the different anti-OVA IgG isotypes, IgG1, IgG2a and IgG2b, as compared to the effects of Quil A, 10 µg, and alum, 300 µg.

Testing of Immune Stimulatory Effects Using Anti-OVA IgG Titers from Immunized Mice Sera Adjuvant effects can be determined by measuring anti-OVA antibody titers by ELISA following immunization with OVA in the absence and presence of adjuvant candidates as follows: BALB/c mice (8-10 weeks old) are immunized subcutaneously three times at two week intervals with one of the following formulations: 10 μg of OVA (Sigma) alone or plus i) an adjuvant of the present invention, 10 to 250 μg doses, or ii) Quil A, 10 μg dose. Control mice are injected with PBS, PBS with OVA or PBS with OVA plus 300 μg of aluminum hydroxide. Sera, are harvested two weeks after the last immunization and the anti-OVA antibody titers determined by ELISA using Immulon II plates coated overnight at 4° C. with 100 μL of an OVA solution (50 μg/ml in PBS). Plates are washed twice with PBS and nonspecific binding prevented by incubating for 1.5 h at 37° C. with 100 μL of 2% casein acid hydrolysate in PBS per well, followed by four washes with 0.05% Tween 20 in distilled water. Sera dilutions from 1:20 to 1:1,562,500 in PBS (100 μL per well) are incubated for 1 h at RT. Plates are washed with 0.05% Tween 20 in distilled water and delivered 100 μL per well of a horse radish peroxidase (HRP) conjugate of goat anti-mouse IgG or IgG1, IgG2a or IgG2b in 2% casein acid hydrolysate diluent and incubated for 30 min at room temperature. Plates are then washed as described before and the extent of peroxidase reaction determined by incubating with 3,3',5,5'-tetramethylbenzidine (TMB) for 10 min at RT, stopping the reaction with 1 N sulfuric acid and measuring the absorbance at 450 nm subtracting the absorbance of the antigen-negative well from the absorbance of each antigen-positive well. The anti-OVA $IgG_{Total}$, IgG1, IgG2a and IgG2b, or immune responses are determined from the end-point titers obtained by plotting the absorbance due to antigen-specific antibody binding as a function of the logarithm of the serum dilution, and the end-point titer estimated from the serum protocol to measure the immune stimulatory effect of Quil A, DS-QS and alum on the production dilution yielding an absorbance of 0.25 (cutoff value). FIG. 4 illustrates the results of use of this of the different IgG isotypes by BALB/c mice.

Figure 5A:
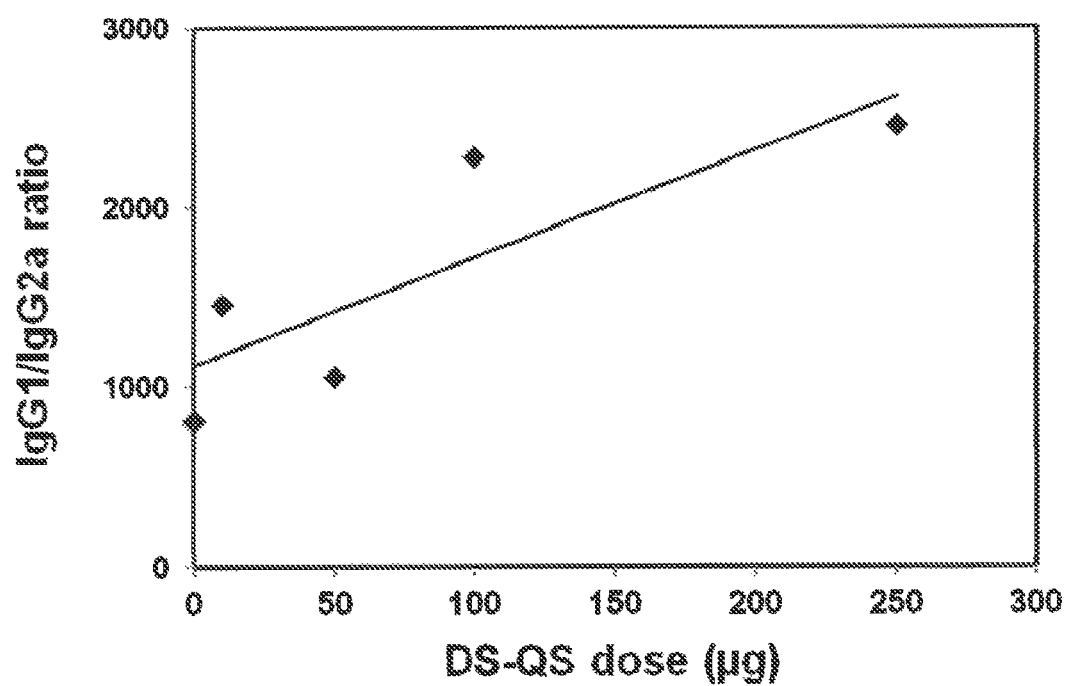
FIG. 5(A) shows the effects of increasing DS-QS doses in the vaccine formulations on the ratio between the anti-OVA IgG1 and IgG2a end point titers (IgG1/IgG2a ratio); a positive slope indicates a Th2 biased immune response. (B) Shows for comparison purposes, the IgG1/IgG2a ratios obtained with OVA alone and with either Quil A, 10 µg, or alum, 300 µg. The decrease in the IgG1/IgG2a ratio from sera of mice immunized with Quil A indicates a Th1 immune response, while the absence of change in the same ratio from sera of mice immunized with alum indicates a Th2 immune response.
Figure 5B:
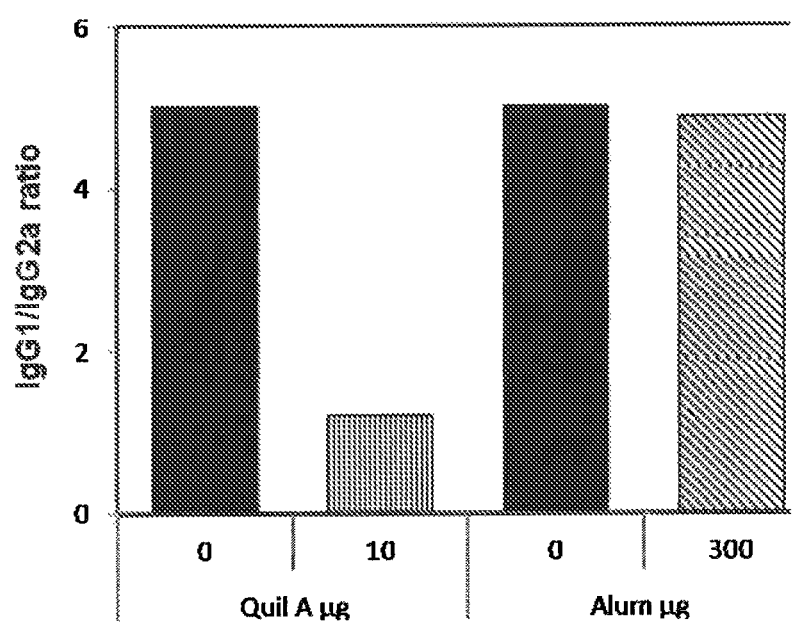

Immune stimulatory agents or adjuvants affect the expression of the different antigen-specific IgG isotypes and in some cases the increase of a specific isotype can be used as an indicator or the immunity type: Th1 or Th2. In BALB/c mice production of IgG2a is dependent on the expression of IFN-γ, a Th1 immunity cytokine, thus increase or decrease of this isotype titers in this mouse strain can be a reliable indicator of the type of immunity stimulated by an adjuvant. The relative increase or decrease of IgG2a production can be assessed by plotting either the IgG1/IgG2a or $IgG_{total}$/IgG2a end-point titers ratio as a function of the adjuvant dose. An increase in IgG2a levels, as shown by a negative slope with increasing adjuvant doses, indicates Th1 immunity, while a positive slope would signify an increase of IgG1 production, an isotype associated to Th2 polarized immunity. FIG. 5-A shows the use of this method to establish that DS-QS stimulate Th2 immunity; however, Quil A (FIG. 5-B), as shown by the decrease in the $\log_{10}$ of the IgG1/IgG2a ratios determined at a 0 and 10 µg doses, stimulates Th1 immunity against OVA, an antigen that has both T and B cell epitopes.

Example 4

Effects of DS-QS and Quil A on Lymphoproliferation Stimulated by OVA

Figure 6:
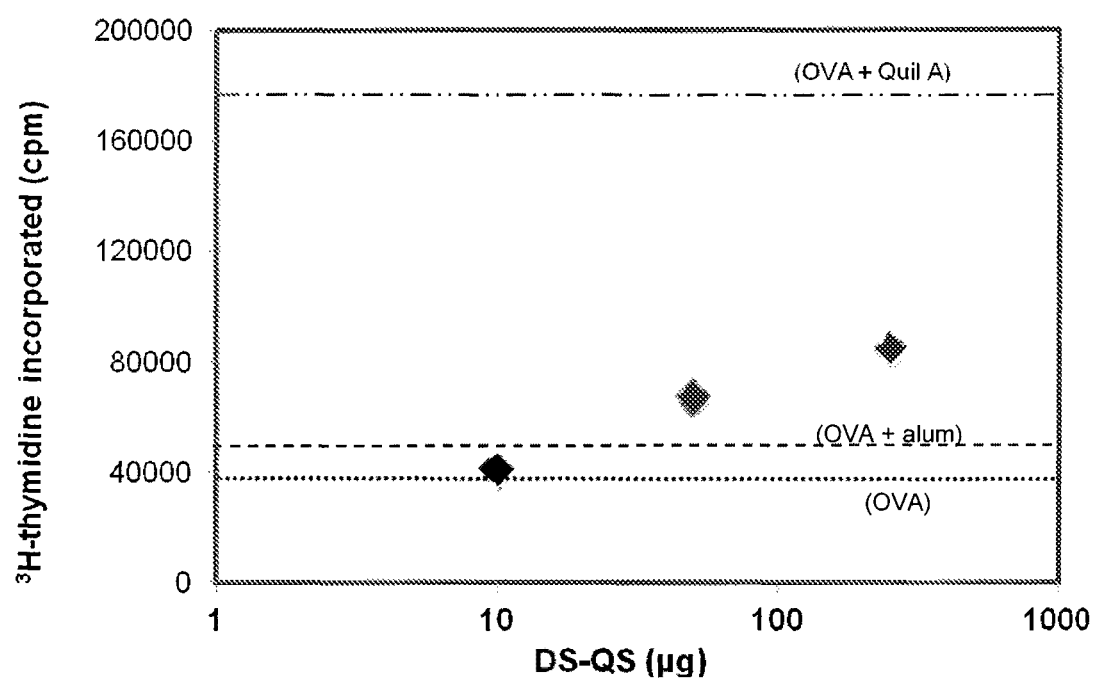
FIG. 6 shows the effects of increasing doses of DS-QS, 10, 50 and 250 µg, on the OVA-stimulated proliferative response of spleenocytes isolated from mice immunized with OVA and the different doses. For comparison purposes, the proliferative response of spleenocytes isolated from mice immunized with OVA alone ( . . . ), with Quil A, 10 µg (- - - -) or, alum, 300 µg (- . . . - . . . ) are indicated.

Single cell suspensions of spleens from control and immunized mice are prepared in complete medium, which consists of RPMI 1640 supplemented with 10% FBS, 2 mM L-glutamine, 10 mM HEPES buffer, 50 mM 2-mercaptoethanol and antibiotics, for cellular assays. Spleen cells, $2 \times 10^5$ per well, from control and immunized mice are cultured in triplicate in 0.2 mL of complete medium in 96-well flat bottom microtiter plates with either medium, 10 µg/mL of OVA or 3 µg/mL of concanavalin A. Cultures are incubated at 37° C. in a humidified, 5% CO2 incubator for 3 days, pulsed with [$^3$H]thymidine, [$^3$H]TdR, for 16 hours, and harvested using a Skatron (Sterling, Va.) semi-automated harvester. Proliferation is determined from the [$^3$H] TdR incorporated and measured by determining the radioactivity in a liquid scintillation counter. FIG. 6 shows the negligible [$^3$H]TdR incorporation in cells derived from mice immunized with OVA and DS-QS, in contrast to those cells derived from animals immunized with OVA and Quil A.

Example 5

Determination of DS-QS and Quil A Effects on IFN-γ and IL-4 Cytokine Production

Figure 7:
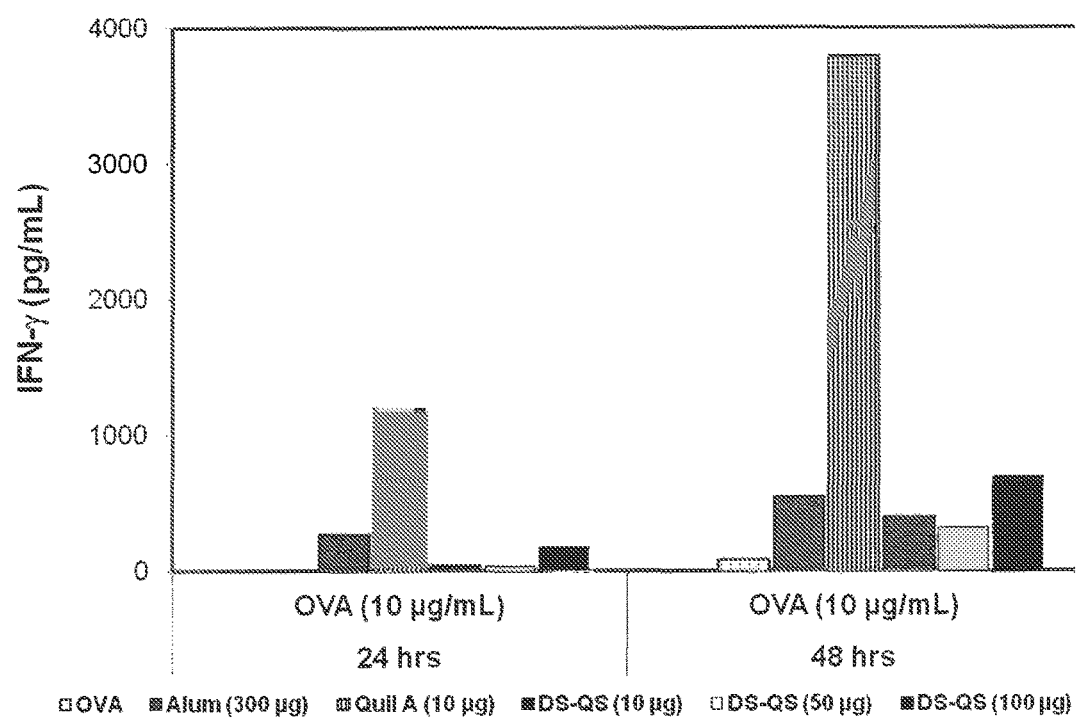
FIG. 7 shows the effects of different adjuvants on the secretion of IFN-γ by spleenocytes isolated from mice immunized with OVA plus alum DS-QS (10, 50 or 100 µg). For comparison purposes the IFN-γ secreted by OVA alone, with alum (300 µg) or Quil A (10 µg) are shown. The secreted IFN-γ stimulated by DS-QS was similar to that stimulated by alum. The produced IFN-γ was measured by ELISA after growing the cells in the presence of OVA (10 µg/mL), for 24 and 48 hours.
Figure 8:
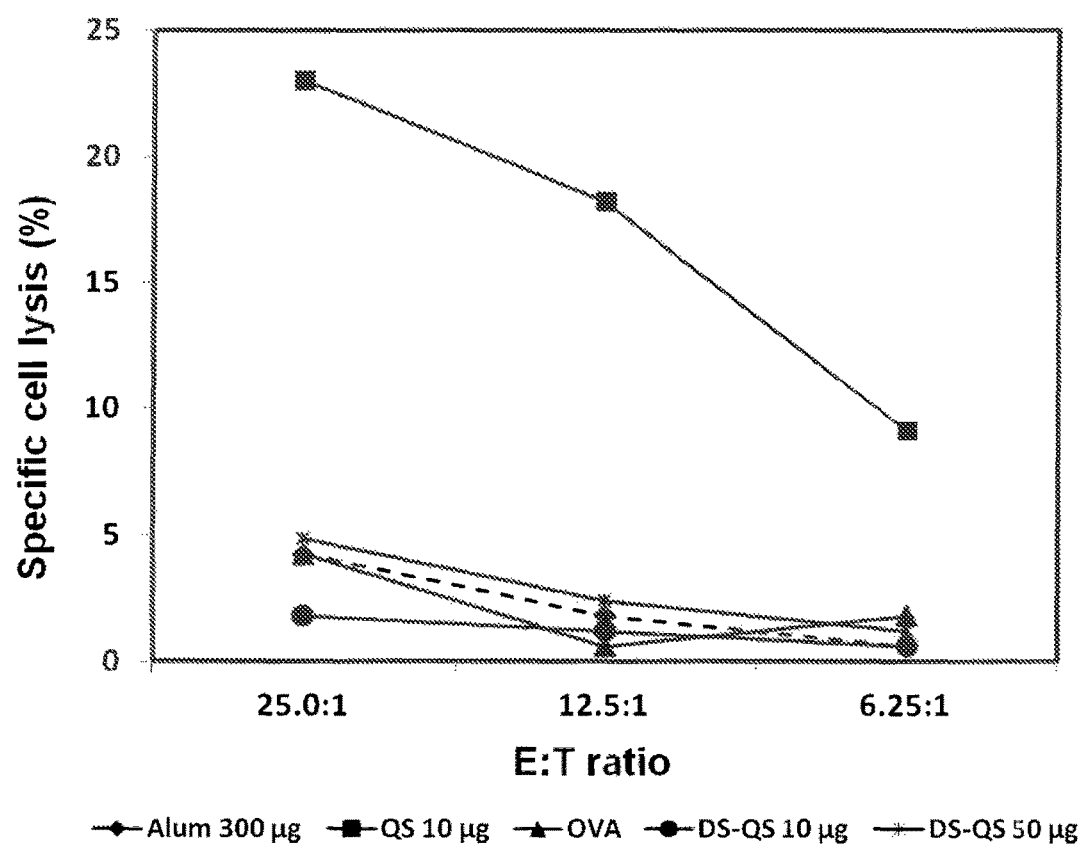
FIG. 8 shows the effects of alum, Quil A (QS), and DS-QS on the production of antigen-specific CTL. C57BL/6 mice were immunized s.c. on days 1, 15 and 29 with OVA (10 µg) alone or in combination with one of the following compounds: alum (300 µg), QS (10 µg) and DS-QS (10 or 50 µg). On day 43, spleens were removed and the CTL activity at various effector:target (E:T) cell ratios determined as described in Example 10.

IFN-γ and IL-4 are cytokines associated with Th1 and Th2 immunity respectively that are produced by antigen-activated T lymphocytes in cell culture and can be determined by ELISA. Mice immunized 3 times every 2 weeks are sacrificed 2 weeks after the last immunization, their spleens harvested and single cell suspensions prepared in complete medium (Marciani D J et al. *Vaccine* 18:3141-3151, 2000). As negative controls spleen cells from mice injected with PBS \only are used. Cells ($2 \times 10^5$ per well) are cultured in 96-wells flat microtiter plates (Costar) with either medium alone or medium containing OVA concentrations ranging from 0.5 to 5 µg/mL (to activate lymphocytes) at 37° C. in humidified air with 5% $CO_2$ for 18, 24 or 48 hours. After the specified incubation time the media is removed, centrifuged to take out cellular debris and the clear supernatant frozen and stored at −20° C. for subsequent assays. Levels of IFN-γ and IL-4 are determined using commercial ELISA kits (Endogen; BD-Pharmigen) according to their instructions and the cytokine levels expressed in pg/mL, FIG. 7 shows the effects of DS-QS and Quil A on the secretion of IFN-γ, confirming that DS-QS stimulates a Th2 immune response.

Example 6

Formulations for Increasing the Production of Antibodies Specific for Aβ Antigens A peptide with the amino acid sequence of Aβ40, Aβ42 or Aβ43, prepared by organic synthesis, is dissolved in physiological phosphate buffered saline solution (PBS) containing 2% mannitol as an stabilizing agent, to give concentrations of 50, 100, 200 and 400 µg/mL of the Aβ antigen. To each of these solutions add an equal volume of PBS containing 40, 200, 400 and 1000 µg/mL of DS-QS, mix and sterilize by filtration; the final solutions having 25, 50, 100 and 200 µg/mL of the Aβ antigen, would also contain each 20, 100, 200 or 500 µg/mL of DS-QS. As controls for Th1 and Th2 immune responses, the Aβ antigen(s) would be formulated with 50 µg/mL of Quil A and 400 µg/mL of alum, respectively. The sterile samples containing DS-QS are stored at 4° C. For evaluation of the different vaccine formulations, 0.5 mL doses are administered intraperitoneal (i.p) to female BALB/c mice, 7-8 weeks old, on days 1, 15 and 30. Blood samples are collected on days 14, 29 and 44, sera is prepared and store frozen for subsequent ELISA determinations; the animals are sacrificed on day 44. The total antibodies and their isotypes IgG1, IgG2a and IgG2b present in sera were determined by ELISA using Immulon II plates coated overnight at 4° C. with 100 µL of an Aβ-antigen solution containing 50 µg/ml in PBS. Plates with aggregated Aβ were prepared by delivering to ea. well 50 µL of the Aβ antigen, 100 µg/ml in water, followed by 50 µL of 0.3 M NaCl in 20 mM Na phosphate buffer pH 7.2, mixing the solutions and coat overnight at 4° C. After the coating procedure, treat the plates as indicated above. Plates are washed twice with PBS and nonspecific binding prevented by incubating for 1.5 h at 37° C. with 100 µL of 2% casein acid hydrolysate in PBS per well, followed by four washes with 0.05% Tween 20 in distilled water. Sera dilutions from 1:20 to 1:1,562,500 in PBS (100 µL per well) are incubated, 1 h at RT, washed, added HRP conjugates of anti-mouse goat IgG and processed and the data analyzed as described in Example 3.

Example 7

Formulations for Increasing the Production of Antibodies Specific for Hyperphosphorylated Tau-Derived Peptide Antigens A peptide with the amino acid sequence of Tau379-408 [P-Ser$_{396,404}$] or Tau417-427[P-Ser$_{422}$], prepared by organic synthesis, free or conjugated to KLH via a linker at the amino terminal, is dissolved in physiological phosphate buffered saline solution (PBS) containing 2% mannitol as an stabilizing agent, to give concentrations of 50, 100, 200 and 400 µg/mL of the tau-derived antigen. To each of these solutions add an equal volume of PBS containing 40, 200, 400 and 1000 µg/mL of DS-QS, mix and sterilize by filtration; the final solutions having 25, 50, 100 and 200 µg/mL of the tau antigen, would also contain each 20, 100, 200 or 500 µg/mL of DS-QS. As controls for Th1 and Th2 immune responses, the tau antigen(s) would be formulated with 50 µg/mL of Quil A and 400 µg/mL of alum, respectively. The sterile samples containing DS-QS are stored at 4° C. For evaluation of the different vaccine formulations, 0.5 mL doses are administered intraperitoneal (i.p) to female BALB/c mice, 7-8 weeks old, on days 1, 15 and 30. Blood samples are collected on days 14, 29 and 44, sera is prepared and store frozen for subsequent ELISA determinations; the animals are sacrificed on day 44. The total antibodies and their isotypes IgG1, IgG2a and IgG2b present in sera were determined by ELISA using Immulon II plates coated overnight at 4° C. with 100 µL of a solution of a conjugated tau-antigen to BSA, containing 50 µg/ml of the tau antigen in PBS. Plates are washed twice with PBS and nonspecific binding prevented by incubating for 1.5 h at 37° C. with 100 µL of 2% casein acid hydrolysate in PBS per well, followed by four washes with 0.05% Tween 20 in distilled water. Sera dilutions from 1:20 to 1:1,562,500 in PBS (100 pit per well) are incubated, 1 h at RT, washed, added HRP conjugates of anti-mouse goat IgG and processed and the data analyzed as described in Example 3.

Example 8

Effects of Non-Ionic Polysorbate Detergents on the Formulations that Increase the Anti-Aβ or Anti-Tau Immune Response To determine the role of non-ionic polysorbate detergents on the immune stimulatory effects of DS-QS and Quil A, the formulations from Examples 6 and 7 are used for immunization, but, in the presence of 4 or 8 mg/mL of Tween-80 or polysorbate 80, (polyoxyethylene (20) sorbitan monooleate). Following the immunization schedules from Examples 6 and 7, total IgG and the isotypes IgG1, IgG2a and IgG2b titers, are determined by ELISA and analyzed following the protocol described in Example 3.

Example 9

Effects of DS-QS and Quil A on the Lymphoproliferation Stimulated by Aβ or Tau-Derived Antigens Animals from Examples 6 and 7, are sacrificed on day 44 and used to prepare single cell suspensions of spleens from control and immunized mice in complete medium, which consists of RPMI 1640 supplemented with 10% FBS, 2 mM L-glutamine, 10 mM HEPES buffer, 50 mM 2-mercaptoethanol and antibiotics, for cellular assays. Spleen cells, $2\times10^5$ per well, are cultured in triplicate in 0.2 mL of complete medium in 96-well flat bottom microtiter plates with either plain medium, or containing 20 µg/mL of Aβ or tau-derived antigens or 4 µg/mL of con A. Cultures are incubated at 37° C. in a humidified, 5% CO2 incubator for 3 days, pulsed with [$^3$H]thymidine, [$^3$H]TdR, for 16 hours, and harvested using a Skatron (Sterling, Va.) semi-automated harvester. Proliferation is determined from the [$^3$H] TdR incorporated and measured by determining the radioactivity in a liquid scintillation counter.

Example 10

Effects of DS-QS on the Production of OVA Specific CTLs

A reliable indicator of Th1 immunity is the antigen-specific CTL production against cells expressing the antigen, used as an immunogen processed by the class pathway for presentation. Availability of the EL4 mouse cell line (C57BL/6 mice) transfected with the OVA gene, E.G7-OVA (MW Moore et al. *Cell* 54:777-785, 1988), allows such assessment. Spleen cells ($2\times10^6$ cells/well) from C57BL/6 mice immunized, i.p. according to the protocol from Example 3 as well as from non-immunized mice and sacrifice on day 44, are added to 24 well plates containing 1 mL of complete medium plus $1\times10^5$ E.G7-OVA cells irradiated with X rays (20,000 R) to stop cell division and incubated for 6 days to yield the effector (E) cells. Target cells (T) are the EL4 (negative control) and E.G7-OVA cells expressing the OVA gene that have been previously incubated for 1 hour with 300 µCi of $^{51}$Cr labeled sodium chromate and washed. Target cells ($1\times10^4$) are incubated with an increasing number of E cells for 6 h. and the amount of $^{51}$Cr released in the supernatant (result of cell lysis by CTLs) measured in a liquid scintillation counter and expressed in counts per mm (cpm). As a control for total lysis, i.e. 100% or maximum release, use $^{51}$Cr labeled E.G7-OVA tai get cells treated with 2% Triton x-100; the negative controls are $^{51}$Cr labeled E.G7-OVA cells treated with medium only and EL4 cells (spontaneous release). Calculate the percent lysis for each E:T ratio using the following formula:

$$\% \text{ lysis} = \frac{(\text{cpm lysis by } CTLs - \text{cpm spontaneous release})}{(\text{cpm 100 \% lysis} - \text{cpm spontaneous release})}$$

Plot percent lysis as a function of the E:T ratio, the positive slope would be proportional to the CTLs' lytic activity. The lysis of EL4 cells by OVA-specific CTLs should be equal to the spontaneous release.

Example 11

Formulations for Increasing the Production of Antibodies Specific for Aβ-Derived Antigens An Aβ-derived peptide with an amino acid sequence such as Aβ1-7 (U.S. Pat. No. 8,034,348 B2); Aβ1-6 attached to a VLP (U.S. Pat. No. 7,279,165 B2); the N-end A042 sequence DAEFH or its mimotopes, free or conjugated to an acceptable carrier (U.S. Pat. No. 8,022,180 B2); Aβ10-21 in all-D or all-L configurations, with a N-terminal and/or C-terminal substituent (US 2002/0094335 A1), prepared by organic synthesis, is dissolved in PBS containing 2% mannitol as an stabilizing agent, to give concentrations of 50, 100, 200 and 400 of the Aβ antigen. These vaccine formulations are administered i.p, to BALM mice, without or with 4 or 8 mg/mL of polysorbate, 40, plus 20, 100, 200 or 500 µg/mL of DS-QS. As a Th1 control, the animals are vaccinated with a similar formulation, but with 50 µg/mL of Quil A instead of DS-QS. Process the samples by ELISA as described in Example 6 for Aβ-antigens, and analyze the data as described in Example 3 by plotting IgG1/IgG2a or IgG$_{total}$/IgG2a titers ratio as a function of the adjuvant dose.

Example 12

Effects of DS-QS and Quil A on the Immune Response Against Aβ-Derived Antigens of Human APP Transgenic Mice Eight months old female APP transgenic mice carrying a human amyloid precursor protein (APP) are injected i.p. with the vaccine formulation as described in Example 6, bleed from the tail vein at days 14, 29 and 44, and after at months 2, 3, 5, 6 and 8 after the first immunization and the antibody titers for each isotype determined by ELISA as described in Example 6. The affinities of the different antibody isotypes for the Aβ-derived antigens are, determined at the same time intervals indicated above using the avidity index, an indicator of the average antibody affinity, measured by ELISA utilizing the ammonium thiocyanate elution method (Pullen G R et al. *J Immunol Methods* 86:83-87, 1986; Marciani D J et al. *Vaccine* 9:89-96, 1991). Briefly, a high binding surface microtiter plate, e.g. Immulon 4HBX or Enhanced Binding plates, both from Thermo Electron Corp. are coated with Aβ-derived antigens as described in Example 6, and the wells are blocked with 10% normal goat serum and washed with 0.05% Tween-20 in water. Immune mouse sera diluted in 10% normal goat serum in PBS to a titer resulting in an $A_{450}$ of 0.5-1.0 in a standard ELISA were incubated in ea. well for 1 hour at RT. Well are washed with 0.05% Tween-20 in water and then incubated with concentrations of ammonium thiocyanate in the range of 0 to 4 M in 0.1 M Na phosphate, pH 6. Remove the thiocyanate solution, wash with 0.1 M Na phosphate buffer, and measure the mouse IgG bound to the Aβ-derived antigen using a goat anti-mouse IgG-HRP conjugate and TMB as a chromogenic substrate. The avidity index, determined from a plot of thiocyante concentration versus $A_{450}$, is expressed as the molarity of a thiocyanate solution that removes enough anti-Aβ antibodies to reduce by 50% the absorbance measured in the absence of incubation with ammonium thiocyanate.

What is claimed is:

1. A vaccine formulation for human or veterinary use, comprising:
   (a) one or more of the following peptides or polypeptides:
      i) Aβ-protein (1-40), Aβ-protein (1-42) or Aβ-protein (1-43); or
      ii) full length tau protein,
   and
   (b) one or more Quillaja desacylsaponins, having a 3-glucuronic acid residue, a quillaic acid as triterpene aglycone core with an aldehyde group at position 4, and lacking an acyl group on the oligosaccharide at the position 28 of the triterpene aglycone,
   wherein the 3-glucuronic acid residue is either alone or linked to a linear or branched oligosaccharide having from one to four glycosyl residues, and the oligosaccharide at position 28 is a linear or branched oligosaccharide having from two to seven glycosyl residues.

2. The vaccine formulation of claim 1, wherein said one or more peptides or polypeptides is Aβ-protein (1-40), Aβ-protein (1-42) or Aβ-protein (1-43).

3. The vaccine formulation of claim 2, wherein said one or more peptides or polypeptides is Aβ-protein (1-40).

4. The vaccine formulation of claim 2, wherein said one or more peptides or polypeptides is Aβ-protein (1-42).

5. The vaccine formulation of claim 1, wherein said one or more peptides or polypeptides is a full length tau protein.

6. The vaccine formulation of claim 5, wherein said peptide is phosphorylated at serine, threonine or tyrosine amino acid residues.

7. The vaccine formulation of claim 1, further comprising a pharmaceutically acceptable carrier or diluent.

* * * * *